US012285788B2

(12) United States Patent
Mellies et al.

(10) Patent No.: US 12,285,788 B2
(45) Date of Patent: Apr. 29, 2025

(54) BACTERIAL COMPOSITIONS AND METHODS OF POLYMER DEGRADATION USING THE SAME

(71) Applicant: Reed Institute, Portland, OR (US)

(72) Inventors: Jay Mellies, Portland, OR (US); Morgan Vague, Portland, OR (US)

(73) Assignee: REED INSTITUTE, Portland, OR (US)

( * ) Notice: Subject to any disclaimer, the term of this patent is extended or adjusted under 35 U.S.C. 154(b) by 1076 days.

(21) Appl. No.: 17/126,566

(22) Filed: Dec. 18, 2020

(65) Prior Publication Data

US 2021/0114069 A1 Apr. 22, 2021

Related U.S. Application Data

(63) Continuation of application No. PCT/US2019/037522, filed on Jun. 17, 2019.
(60) Provisional application No. 62/686,560, filed on Jun. 18, 2018.

(51) Int. Cl.
| | | |
|---|---|---|
| C12N 1/20 | (2006.01) | |
| B09B 3/00 | (2022.01) | |
| B09C 1/06 | (2006.01) | |
| B09C 1/08 | (2006.01) | |
| B09C 1/10 | (2006.01) | |
| C12P 1/04 | (2006.01) | |

(52) U.S. Cl.
CPC .......... *B09B 3/00* (2013.01); *C12N 1/20* (2013.01); *B09C 1/06* (2013.01); *B09C 1/08* (2013.01); *B09C 1/10* (2013.01); *C12P 1/04* (2013.01)

(58) Field of Classification Search
None
See application file for complete search history.

(56) References Cited

U.S. PATENT DOCUMENTS

| | | |
|---|---|---|
| 7,736,879 B2 | 6/2010 | Kumar et al. |
| 2016/0280881 A1 | 9/2016 | Boisart et al. |

FOREIGN PATENT DOCUMENTS

| | | | | |
|---|---|---|---|---|
| CN | 106399153 A | 2/2017 | | |
| WO | WO-2010075609 A1 * | 7/2010 | ............. | B29B 17/04 |
| WO | 2019245986 A1 | 12/2019 | | |

OTHER PUBLICATIONS

Gogoi et al., Aquaculture effluent treatment with ammonia remover Bacillus albus, J. Environ. Chem. Eng. 9, 2021, 105697. (Year: 2021).*
Vimala et al., Biodegradation of polyethylene using biosurfactants, national Conference on Technological Trends, 2015. (Year: 2015).*
Sen et al., Microbial degradation of low density polyethylene (LDPE), J. Env. Chem. Eng. 3, 2015, 462-73. (Year: 2015).*
Roberts et al., Environmental Consortium Containing *Pseudomonas* and *Bacillus* Species Synergistically Degrades Polyethylene Terephthalate Plastic, mSphere 5, 2020, e01151-20. (Year: 2020).*
Davis, Antibiotic discovery throughout the Small World Initiative, MicrobiologyOpen, 6, 2017, e435. (Year: 2017).*
International Search Report and Written Opinion dated Sep. 17, 2019 for International Application PCT/US2019/037522, Sep. 17, 2019, 16 pages.
Kyaw, et al., "Biodegration of Low Desnity Polythene (LDPE) by *Pseudomonas* Species", Indian J Microbiol, 52(3), Feb. 5, 2012, pp. 411-419.
Nakkabi, Asmae, et al., "Biodegradation of Poly (Ethylene Terephthatate) by Bacillus Subtilis", International Journal of Recent Advances in Multidisciplinary Research, Vo. 02, Issue 12, Dec. 2015, pp. 1060-1062.
Pathak, et al., "Review on the current status of polymer degradation: a microbial approach", Bioresour, Bioprocess 4:15, Dec. 2017, 31 pages.
Extended European Search Report dated Aug. 10, 2021 for EP application 19822608.6.
Nakkabi, et al., "Biodegradation of Poly (Ethylene Terephthalate) by Bacillus Subtilis", International Journal of Recent Advances in Multidisciplinary Research, vol. 02, No. 12, Dec. 1, 2015 (Dec. 1, 2015), pp. 1060-1062.
Vatseldutt, et al., "Isolation and Characterization of Polythene Degrading Bacteria from Polythene Dumped Garbage", Int. J. Phar. Sci. Rev. Res. Mar-Apr International Journal of Pharmaceutical Sciences Review and Research, Dec. 31, 2014 (Dec. 31, 2014), pp. 205-206.
Ziaullah, et al., "Degradation of polyester polyurethane by an indigenously developed consortium of *Pseudomonas* and *Bacillus* species isolated from soil", Polymer Degradation and Stability, vol. 134, Dec. 1, 2016 (Dec. 1, 2016) pp. 349-356.
Asmita, et al., Isolation of Plastic Degrading Micro-organisms from Soil Samples Collected at Various Locations in Mumbai, India, International Research Journal of Environment Sciences, Mar. 2015, 9 pages.

* cited by examiner

*Primary Examiner* — Todd M Epstein
(74) *Attorney, Agent, or Firm* — Stoel Rives LLP

(57) ABSTRACT

Methods of degrading a polymer are provided. The methods may include incubating the polymer with *Pseudomonads* and/or *Bacillus* species and/or bacterial consortia thereof. Kits for degrading a polymer are also provided. The kits may include *Pseudomonads* and/or *Bacillus* species and/or bacterial consortia thereof. The kits may also include an incubator for culturing the *Pseudomonads* and/or the *Bacillus* species and/or bacterial consortia thereof. Compositions for degrading a polymer-containing substrate including the *Pseudomonads* and/or *Bacillus* species and/or bacterial consortia thereof are also provided.

18 Claims, 11 Drawing Sheets
Specification includes a Sequence Listing.

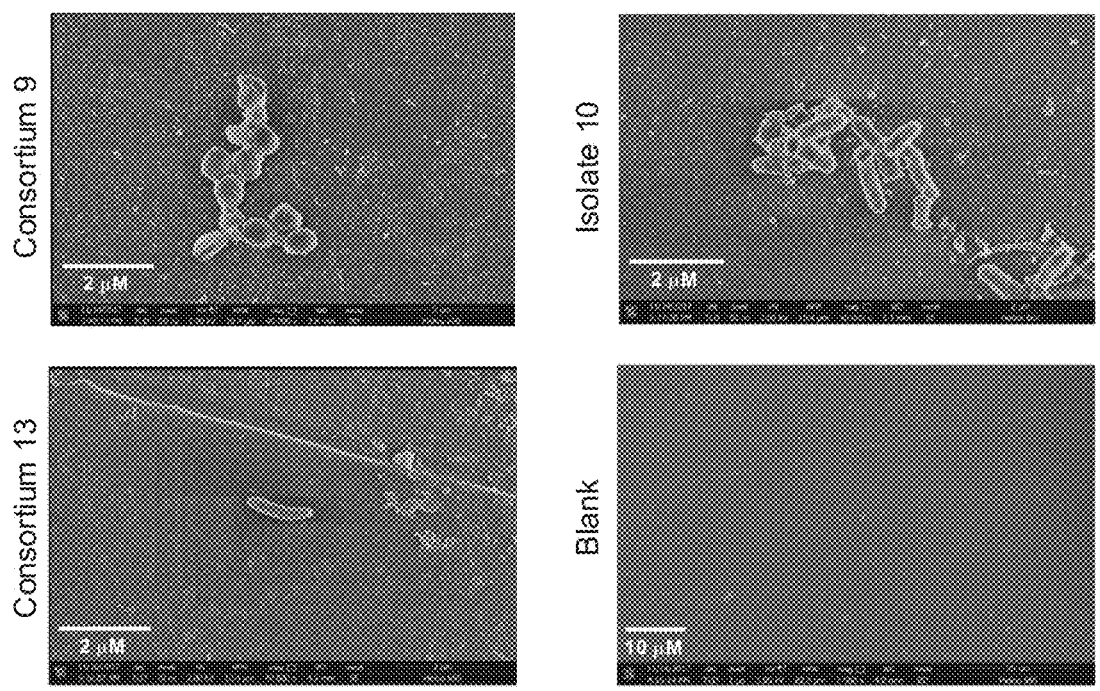
FIG. 6A
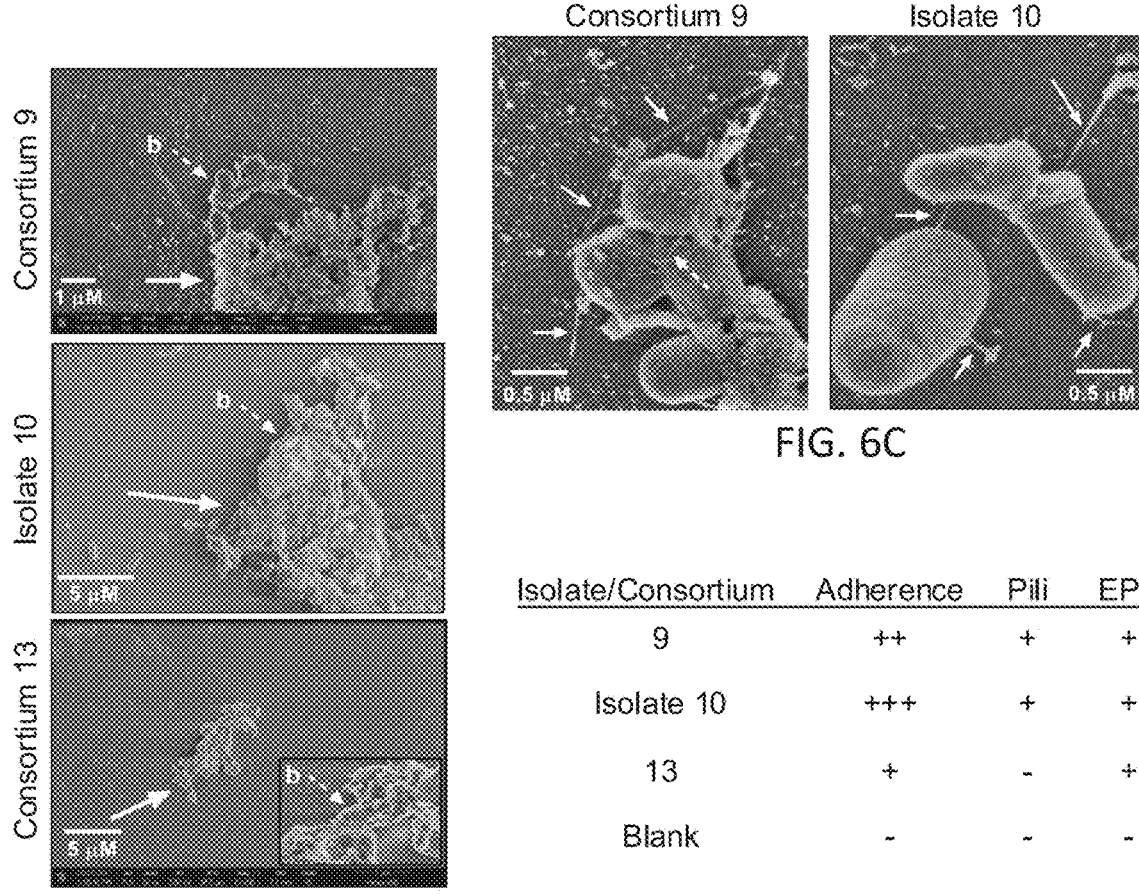
FIG. 6B
FIG. 6C
FIG. 6D

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
actcctacgg gaggcagc                                                 18

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtgccsgcmg ccgcggtaa                                                19

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aaggaggtga tccagcc                                                  17

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
aggcccggga acgtattcac                                               20
```

BACTERIAL COMPOSITIONS AND METHODS OF POLYMER DEGRADATION USING THE SAME

CROSS-REFERENCE TO RELATED APPLICATIONS

This application is a continuation of International Patent Application No. PCT/US2019/037522 filed on Jun. 17, 2019, which claims the benefit of U.S. Provisional Patent Application No. 62/686,560, filed on Jun. 18, 2018, the contents of each of which are hereby incorporated herein by reference in their entireties.

TECHNICAL FIELD

The present disclosure relates generally to methods of degrading polymers using bacteria. The present disclosure also relates to compositions for degrading polymer-containing substrates. The bacteria may include *Pseudomonads* and/or *Bacillus* species.

BACKGROUND

It is estimated that 300 million tons of plastic waste is generated each year, with 30-33 million of that originating in the U.S. alone (see Geyer R, et al. 2017. Sci Adv 3:e1700782). This number, however, underestimates the plastic burden currently befalling the planet as it does not reflect the millions of tons of waste that go unreported each year (see Orhan Y B, Hanife. 2000. International biodeterioration and biodegradation 45:49-55). The plastics industry is projected to continue its growth, with profits expected to exceed $375 billion by 2020 as plastic begins to overtake the medical device sector, and single-use food and beverage packaging continues to dominate the international food landscape (see Research Z. 2016. Plastic Packaging (Rigid Plastic Packaging and Flexible Plastic Packaging) Market for Food & Beverages, Industrial, Household Products, Personal Care, Medical and Other Applications—Global Industry Perspective, Comprehensive Analysis, Size, Share, Growth, Segment, Trends and Forecast, 2014-2020).

Over 50% of plastic produced internationally in 2014 went toward single-use plastic food and beverage packaging, which was quickly discarded as waste rather than recycled (id.). This plastic waste then accumulates in landfills and oceans, where it persists for centuries. In fact, of the 8.3 billion metric tons of plastic that have been produced since plastic's mass introduction to the consumer market following World War II, roughly 6.3 billion metric tons are estimated to have become plastic waste, with 79% accumulating in landfills and 19% ending up in the oceans (see Geyer R, et al. 2017. Sci Adv 3:e1700782). This number is likely an underrepresentation of the plastic currently residing in the oceans as environmental researchers have recently determined that the majority of plastic debris in the ocean resides in deep sea sediments, which act as a plastic sink (see Woodall L C, et al. 2014. R Soc Open Sci 1:140317).

Plastics are typically derived from non-renewable resources such as natural gas, oil, and coal. In the case of polyethylene (PE), the double bonds in ethylene monomers are broken and bond together to form long chains of polyethylene numbering in the thousands of monomers, using a process of heat and pressure. PE and its derivatives are unreactive at room temperature, chemically inert, and possess a high molecular weight and branched 3D structure. PE derivatives are also hydrophobic, which reduces its availability as a carbon source for microorganisms to consume (see Hadad D, et al. 2005. J Appl Microbiol 98:1093-100). These qualities, along with PE's dearth of functional groups easily recognized by bacterial enzymes, make PE and its derivatives largely resistant to biodegradation. Thus PE and its derivatives persist in the environment for anywhere from 200-1,000 years, depending on polymer type (see Ramesh V K, et al. 2011. African Journal of Microbiology Research 5(28):5013-5018).

Polyethylene terephthalate (PET) is a polyethylene plastic derivative consisting of repeating carbon, hydrogen, and oxygen monomers. PET has a non-branched chemical structure and a high ratio of aromatic components that increase its durability and are chemically inert, making it highly resistant to degradation (see Yoshida S, et al. 2016. Science 351:1196-9). Its rigidity and ability to form an effective gas barrier against molecular oxygen makes it popular for use in water bottle and single-serving containers. It is also used in common household goods such as carpet fibers, curtains, and fabrics.

Biodegradation is the process by which microorganisms, usually bacteria or fungi, induce polymer degradation via assimilation or the release of enzymes that can cleave various bonds within the polymer backbone. Spontaneous hydrolysis, photo-oxidation, and mechanical separation of plastic can enhance biodegradation by introducing cleavable bonds or simply increasing plastic surface area for colonization (see Pettigrew C A P, A. C. 1992. Bioscience 42:680-685). Generally, any microorganism capable of reducing plastic polymers to $CO_2$ and water (aerobic conditions), $CO_2$ and methane (anaerobic conditions), or inorganic molecules and biomass is considered to be capable of biodegradation. While it is known that certain bacteria can degrade certain plastics, little has been done to investigate how bacterial consortia and/or compositions containing bacteria capable of polymer degradation might be utilized for bioaugmentation purposes, to mitigate PET waste, or pollution from related plastics.

BRIEF DESCRIPTION OF THE DRAWINGS

The embodiments disclosed herein will become more fully apparent from the following description and appended claims, taken in conjunction with the accompanying drawings.

In FIGS. 4A-4D, error bars represent +/−standard error of the mean and *p<0.05, p<0.01, and *p<0.001 calculated using Student's t-test in relation to the negative control *E. coli* MC4100.

FIG. 6A is a series of scanning electron microscope (SEM) micrographs assessing biofilm formation on PET. PET strips were incubated in carbon-free media inoculated with lipase positive consortia and isolate and imaged with SEM. Colonization of PET plastic by consortia 9, 13, and isolate 10 are shown. Virgin PET (blank) shows no adherence or other hallmarks of bacterial colonization such as in FIG. 6B below.

FIG. 6B is a series of SEM micrographs showing extracellular polymeric substance (EPS) deposits (solid white arrows) secreted as part of biofilm formation. Individual bacteria ("b", dashed arrow) can be seen embedded in the EPS, which can give biofilms their structural integrity.

FIG. 6C is two SEM micrographs showing pili formation by consortium 9 and isolate 10, which can aid in bacterial adherence and biofilm formation. Solid white arrows denote pili attached to PET plastic while dashed arrow denotes a pilus between bacteria, aiding in cell-cell adhesion.

FIG. 6D is a chart summarizing the biofilm morphology observed in SEM images of each consortium and isolate 10. For pili and EPS, (+) denotes presence and (−) denotes absence of given structure. For adherence, each consortia and isolate 10 were graded from excellent adherence (+++) to poor but observable adherence (+).

FIG. 9A depicts Day 0 and Day 50 qualitative images for each treatment indicated to the right of each pair of images. FIG. 9B shows change in weight over the 6-week time period. The granular PET weight loss from the full consortium (FC; Least Square Means$_{full\ consortium}$: 3.15 mg; SD: 0.07) treatment was statistically significantly greater than consortium 9 (C9), consortium 13 (C13), and individual isolates (*p<0.0001).

In FIG. 10B, light microscopy, at 200× magnification, illustrates clear degradation in the inoculated, versus uninoculated sample.

DETAILED DESCRIPTION

Figure 1:
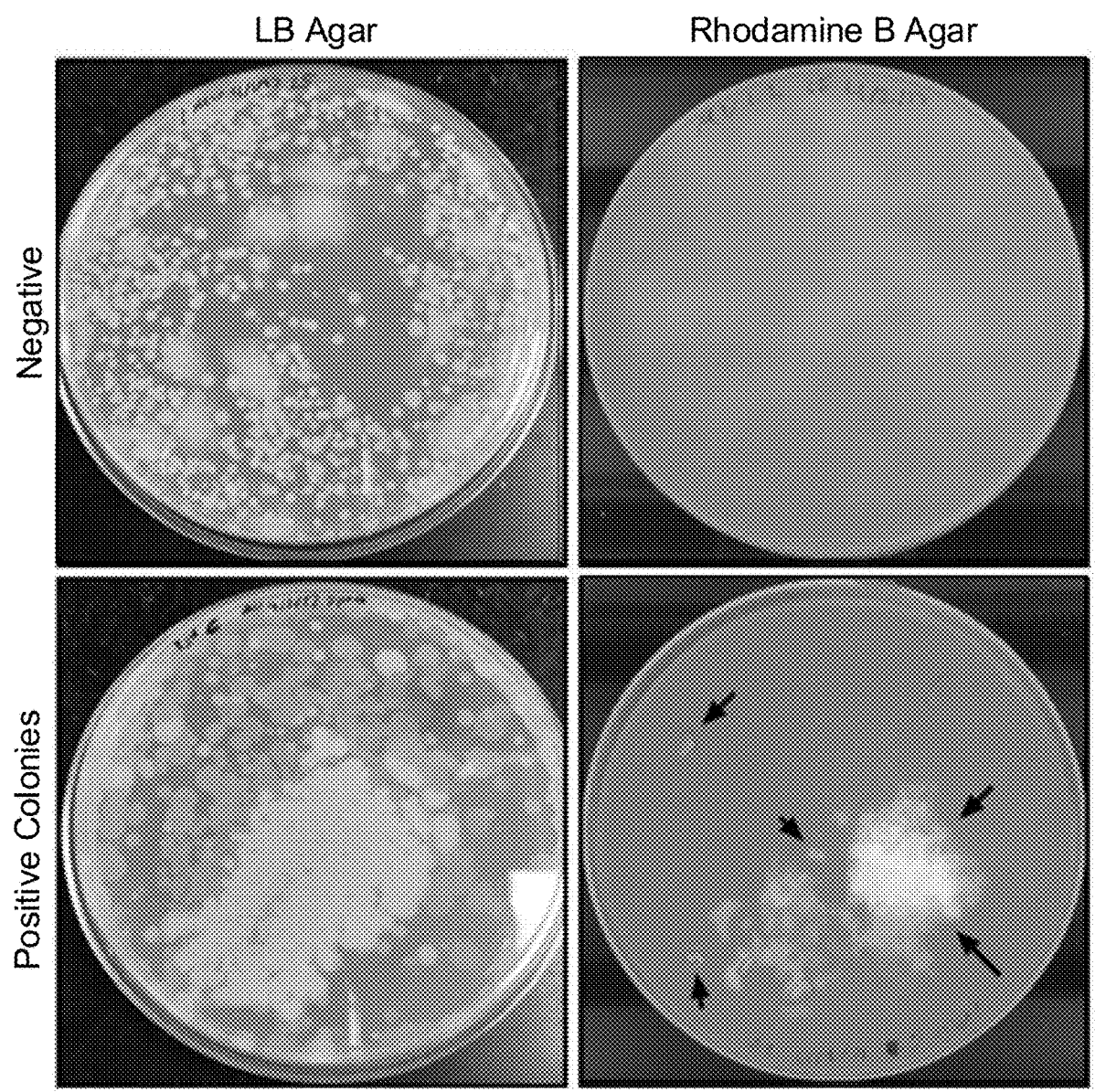
FIG. 1 shows rhodamine B agar tests for lipase activity. Master plates of mixed colonies were generated by soaking soil samples in water and collecting the supernatant to spread on lysogeny broth (LB) plates. Individual plates with growth (representative plates in the top left and bottom left panels) were stamped onto rhodamine B plates (top right and bottom right panels) to screen for lipase activity. The presence of orange or yellow halos under 365 nm ultraviolet (UV) exposure indicated lipase positive colonies (indicated with arrow). After, individual colonies in lipase positive areas were spotted onto new rhodamine plates to isolate the lipase producers and positive spots were re-streaked onto LB for purification.

The present disclosure relates generally to methods of degrading a polymer. The methods may include incubating or combining the polymer with one or more *Pseudomonads* and/or one or more *Bacillus* species. The present disclosure also relates to kits for degrading a polymer. The kits may include one or more *Pseudomonads* and/or one or more *Bacillus* species. The kits may also include an incubator for culturing the one or more *Pseudomonads* and/or the one or more *Bacillus* species. Furthermore, the present disclosure relates to bacterial compositions including the *Pseudomonads* and/or *Bacillus* species for use in degrading a polymer-containing substrate. The present disclosure also relates to lipase-positive bacterial isolates, lipase-positive bacteria consortia, compositions having lipase-positive activity, and combinations thereof, for use in degrading a polymer or a polymer-containing substrate.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

Unless specifically defined otherwise, the technical terms, as used herein, have their normal meaning as understood in the art. The following terms are specifically defined with examples for the sake of clarity.

As used herein, "a" and "an" denote one or more, unless specifically noted.

As used herein, "about" refers to a quantity, level, value, number, frequency, percentage, dimension, size, amount, weight, or length that varies by as much as about 30%, about 25%, about 20%, about 15%, about 10%, about 9%, about 8%, about 7%, about 6%, about 5%, about 4%, about 3%, about 2%, or about 1% to a reference quantity, level, value, number, frequency, percentage, dimension, size, amount, weight, or length. In any embodiment discussed in the context of a numerical value used in conjunction with the term "about," it is specifically contemplated that the term "about" can be omitted.

Without being bound by any one particular theory, it was hypothesized that bacteria in polluted environments are more likely to adapt to harnessing pollutants in order to survive. Accordingly, soil samples were collected from eight different sites along the Gulf Coast of Southeast Texas and within the greater Houston area. The Gulf Coast region of Texas includes multiple EPA Superfund Sites, petroleum refineries, and beaches such as Galveston Bay, into which hundreds of gallons of oil are spilled every day (see Tresaugue M. 2014. Oil spills are a routine occurrence: Since the late 90s, Galveston Bay has averaged 285 spills a year. Houston Chronicle. Hearst Newspapers, Houston, TX).

Sample 1 was collected at the Jones Road Chemical Plume Superfund Site at 1160 Jones Road, Houston, TX (11 Superfund sites exist in the greater Houston, TX area). The Jones Road Superfund Site is currently home to a large strip mall and apartment complex despite high levels of tetrachloroethylene, petroleum, and isoparaffin-like synthetic petroleum-based dry-cleaning solvents in the soil (see DePrang E. 2007. Superfun with Superfund: A scenic tour of Harris County's 11 best toxic attractions. The Texas Observer, Austin, TX). Sample 2 was collected at the Many Diversified Interests Superfund Site at 3617 Baer St, in $5^{th}$ Ward, Houston, TX This Superfund Site had been home to a large foundry and steel manufacturing plant for 70 years, and high levels of heavy metal deposits and petroleum byproducts from manufacturing are present in 34% of $5^{th}$ Ward homes (id.). Samples 3, 4, and 5 were collected at various locations within the Pasadena Refining System at 111 Red Bluff Road. The Pasadena Refining System is a large oil and petrochemical industrial complex sprawling 463 acres along the Houston Ship Channel and is located adjacent to the main oil pipelines that supply the East Coast and Central States of the U.S. The Pasadena Refining System processes roughly 106,000 barrels of crude oil per day (see U.S.A. P. 2017. Operations: Refining, on Petrobas. http://www_petrobras_com/en/countries/u-s-a/operations/. Accessed Oct. 21, 2017). Sample 3 was collected in a parking lot at the entrance, Sample 4 was collected adjacent to the main oil pipeline, and Sample 5 was collected just outside the gates of the refinery complex.

Sample 6 was collected at the West Park Power Station in Houston, TX and Sample 8 was collected from the topsoil outside of the transformers of the Baer Road Power Station, Houston, TX. These power stations have many buried wires; most of which are coated in polyurethane plastic or petroleum-based insulation coating (see Benjamin K. 2016. Insulated Wire, What's Protecting Your Cable?, on Performance Wire and Cable https://www_performancewire_com/insulated-wire-protection). Sample 7 was collected six inches beneath the beach surface at East Beach, Galveston, TX, roughly 12 yards from the shoreline. Samples were collected from various locations in Southeast Texas and brought back to Portland, OR for subsequent propagation and screening in a lab.

Bacterial isolation began by soaking soil samples in PBS, pH 7.4, and shaking on a rotary shaker (225 rpm, 37° C.). The soil sediment was allowed to settle out and the supernatant was then spread onto LB agar plates. These plates were then incubated at 26° C. to favor the growth of environmental isolates. Multiple plates were made from each soil sample to thoroughly investigate the bacterial population native to each location. To screen as many isolates as possible, the master plates of LB agar growth were colony-stamped directly onto rhodamine B agar plates, allowed for grow, and subjected to 365 nm UV light to visualize lipase activity (see FIG. 1). For rhodamine B plates, olive oil was used as a source of long-chain fatty acids to check for lipase activity. Rhodamine B dye binds to free fatty acids (cleaved by a secreted lipase) and glows when exposed to UV radiation (see FIG. 1, lower right panel). Thus, the presence of glowing halos around the colonies is indicative of lipase activity. Colonies that appeared lipase-positive by stamping were isolated and re-tested in order to confirm lipase activity and to isolate pure cultures. In total, 192 colonies were spot-tested after appearing lipase-positive (or growing near alipase-positive organism) during initial rhodamine B screening.

Figure 2A:
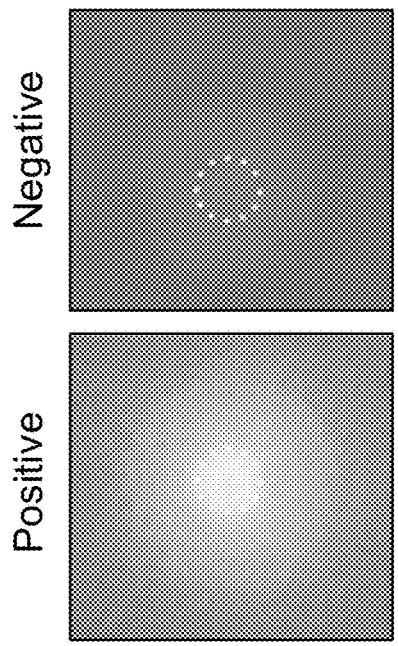
FIG. 2A shows representative negative (top) and positive (bottom) spots on rhodamine B agar. The white, dashed circle delineates the original inoculated area.
Figure 2B:
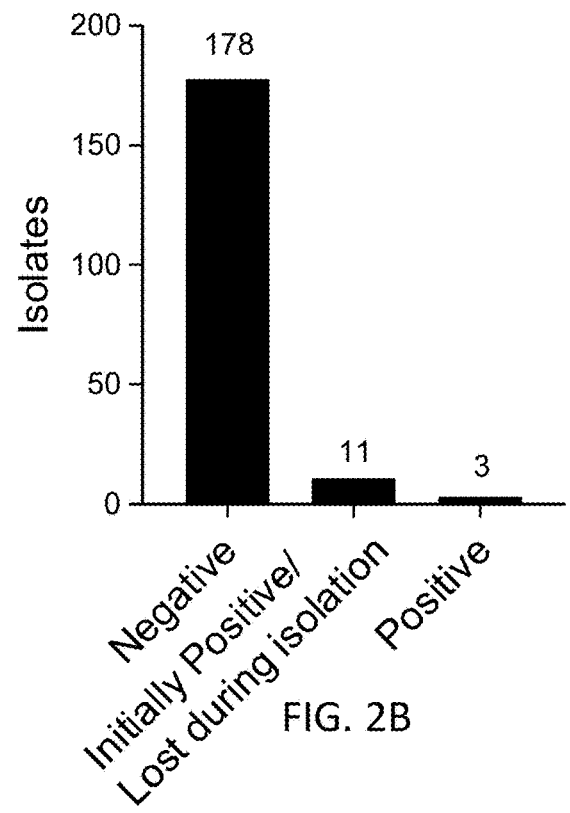
FIG. 2B is a graph showing the total number of isolated lipase-positive and lipase-negative isolates tested.
Figure 2C:
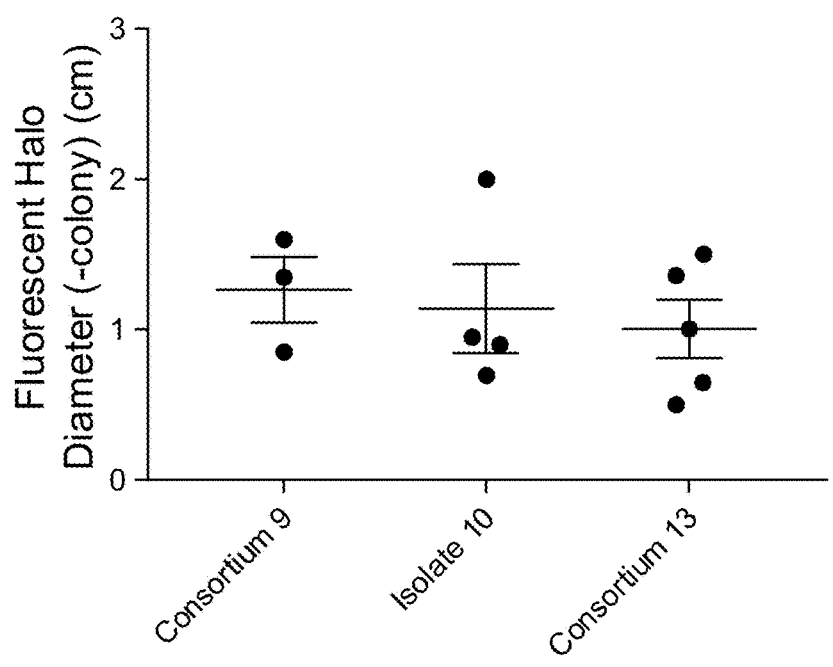
FIG. 2C is a graph showing the results of isolated positive consortia and isolate that were retested multiple times for confirmation of lipase activity. Isolate 10 and consortia 9 and 13 were grown overnight, spotted, and imaged using 365 nm UV light. Error bars represent +/−standard error.

Between the initial screening and spot-testing colonies, a new formulation of rhodamine B agar was adopted that uses 10% of the dye and shows increased sensitivity. Example positive and negative colonies are shown in FIG. 2A. Of the 192 colonies spot-tested, 14 were positive and three consortia remained positive after multiple rounds of spotting and streaking for isolation (see FIG. 2B). By Gram staining, lipase positive colonies consisted of multiple, Gram-negative and Gram-positive bacteria. Eleven (11) of the 14 colonies that were initially positive lost the lipase-positivity during the isolation process and were therefore dropped from this study. Isolate 10 and two consortia, 9 and 13, were tested multiple times to confirm the presence of lipase production (see FIG. 2C).

Figure 3:
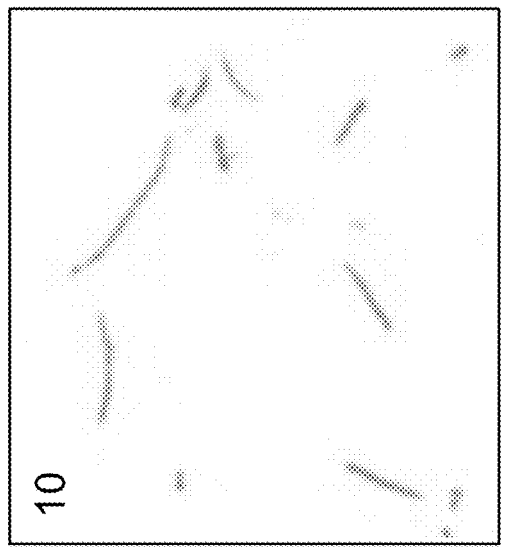
FIG. 3 shows Gram stains of pure isolates from lipase-positive consortia. Lipase-negative isolates were both Gram positive rods (left; 9.1 and 13.1), while all three lipase-positive isolates were Gram negative rods (right; 9.2, 10, and 13.2). Isolates 10 and 13.2 were more elongated rods than isolate 9.2.
Figure 3:
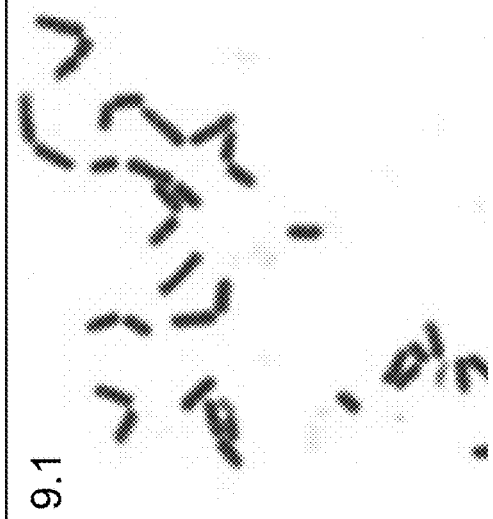
Figure 4A:
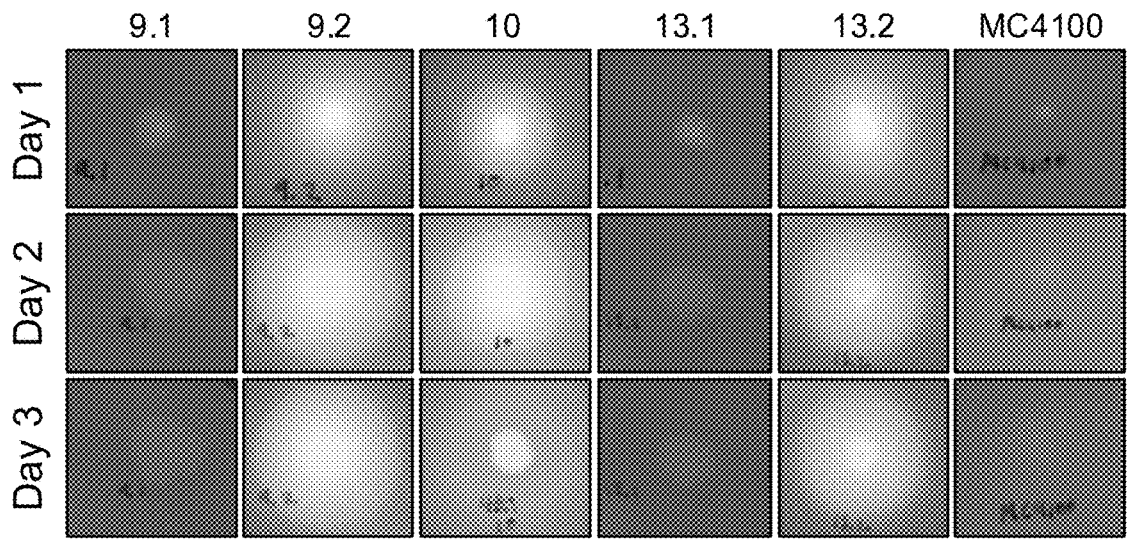
FIG. 4A shows representative images of rhodamine B agar testing over three days to identify lipase positive isolates. Included is a known negative control *E. coli* MC4100.
Figure 4B:
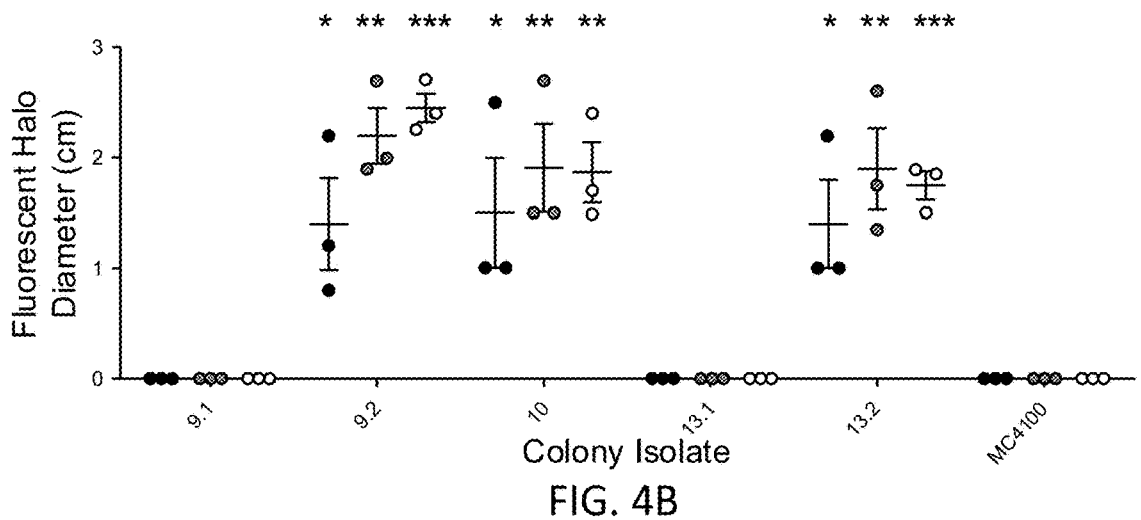
FIG. 4B is a graph showing diameters that were measured one (black), two (grey), or three (white) days post-inoculation for all pure isolate members of positive consortia and the negative control.
Figure 4C:
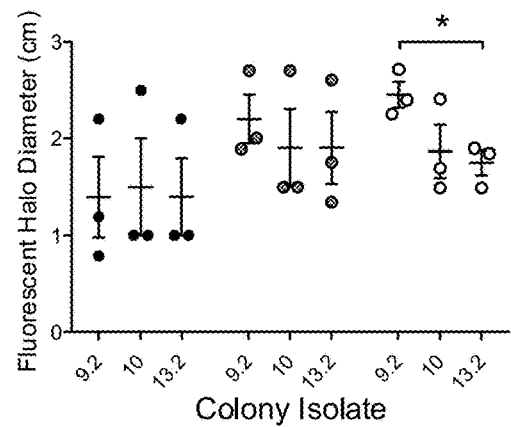
FIG. 4C is a graph showing relative sizes of fluorescent halos on each day for the positive isolates. The color scheme follows as in FIG. 4B. Only one isolate was significantly larger on day three.
Figure 4D:
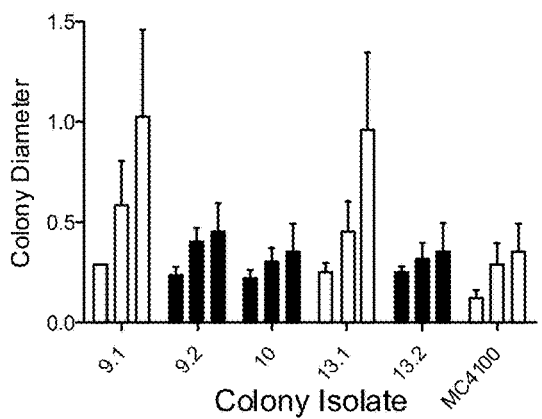
FIG. 4D is a graph indicating that lipase negative results were not because of an inability to form colonies on the rhodamine B agar. Lipase positive isolates are shaded black.

Next, each consortium was repeatedly streaked for isolation and tested via serial Gram stains for purity until pure isolates were obtained (see FIG. 3). Initial Gram stains indicated the cultures were mixed, and colony morphology on the LB plates streaked for isolation was not uniform.

Therefore, attempts to isolate the lipase positive strain were made. From consortium 9, two isolates were purified, a Gram-negative rod (isolate 9.2; deposited as NRRL No. B-67633) and a Gram-positive rod (isolate 9.1; deposited as NRRL No. B-67632). From consortium 13, two isolates were also purified, a Gram-negative rod (isolate 13.2; deposited as NRRL No. B-67634) and a Gram-positive rod (isolate 13.1; deposited as NRRL No. B-67631). Consortium 10 eventually had a single morphology by Gram stain indicating the consortium had been purified down to a single isolate (isolate 10; deposited as NRRL No. B-67630). The other components of the consortium were lost rather than isolated in this case. Overall, the rhodamine B screen using master plates allowed for screening of thousands of colonies for lipase positivity, but any positive cultures are likely mixed and must be isolated by streaking to pure culture, tracking progress using Gram staining, light microscopy, and colony morphology.

With reference to FIGS. 4A-4D, the rhodamine B agar screen of purified environmental isolates identified three lipase positive bacterial strains. Each consortium was separated (e.g., consortium 9 into isolate 9.1 and 9.2) and tested separately for lipase activity. In all cases, one was lipase positive and the other isolate was not. Consortium 10 was purified by serial streaking for isolation into one single isolate. Isolates 9.2, 13.2, and 10, all Gram-negative rods, tested positive for lipase activity suggesting that they were the microorganisms that could be capable of plastic degradation in their respective consortia (see FIGS. 4A and 4B). Isolates 9.1 and 13.1 were lipase negative and therefore less informative to further experiments. Previously, the diameter of fluorescent halos in the rhodamine B assay had been determined to be linearly proportional to the amount of lipase activity in a sample (see Kouker G, et al. 1987. Appl Environ Microbiol 53:211-3). Thus, it was informative to not only know if positive, but how positive each isolate was. Therefore, halo diameters were measured and compared over the course of three days. There were no significant differences between the halo sizes on days 1 and 2. On day three, the halo from isolate 9.2 was significantly larger than that of isolate 13.2 ($p=0.022$) and trending towards larger than isolate 10 ($p=0.11$), suggesting it may harbor a more active lipase (see FIG. 4C). As a control, colony diameters over the three days were taken to ensure that any negative results were not because of an inability to grow on the rhodamine B agar (see fluorescent halos in FIG. 4A). While the lipase-negative isolates appeared to grow better than the lipase positive isolates, isolates 9.1 and 13.1 grew relatively larger colonies on LB agar as well. Thus, without being bound by any one particular theory, it is likely that this phenotype is rather a morphological characteristic unique to colony formation of isolates 9.1 and 13.1 rather than a specific response to rhodamine B agar. Additionally, the negative control (*E. coli* MC4100) formed a colony and was lipase negative by the rhodamine B agar assay (see FIG. 4A). These results confirm that the rhodamine B agar test can not only be used to identify lipase-positive, and putative plastic degrading bacteria, but also presumptively highly active lipases.

Identification of pure isolates was done by 16S rRNA gene sequencing. Primers were used to amplify a ~900 bp fragment of the 16S rRNA gene using direct colony PCR. PCR products were cleaned and sent for sequencing using both forward and reverse primers to achieve paired-end sequences. This helped ensure 100% confidence in the sequence used for genus identification, particularly when one or two base pair changes can be the difference between identity matches. Sequencing was performed at ACGT™ using the Sanger sequencing method and aligned using BIOEDIT™ software to define a core consensus sequence between paired end reads. Paired end reads were obtained from both the forward and reverse primers. Then, the sequence obtained from the reverse primer was reverse-complemented and overlaid with the forward primer sequencing data. The core sequence length varied depending on the quality and agreement of the sequencing reads. Once core sequences were determined, they were entered into nucleotide BLAST®, which compares input nucleotide sequences against all known nucleotide sequences in the National Center of Biotechnology Information (NCBI) database in order to find optimal alignment. Using 16S sequencing, identification at the genus level is possible for most microorganisms, but generally not at the species level due to a lack of sequence variation between related species.

All three lipase-positive isolates were identified as *Pseudomonas* with 100% identity. Isolate 9.2 and isolate 10 were sequenced from PCR amplification of pure isolates while isolate 13.2 had been previously identified from sequencing consortium 13. Sequencing of consortia 9 and 10 were also performed prior to sequencing isolates 9.2 and 10 and BLAST® results matched those of individual isolates. While 16S sequencing is generally not reliable in identification at the species level, it is important to note that the alignments and BLAST® results indicate these are different *Pseudomonas* species, particularly isolate 9.2. While all species alignments in BLAST® were from the genus *Pseudomonas*, they had no overlap with the various species of *Pseudomonas* identified as possibilities in isolate 10 or consortium 13. Taken together with the different Gram stain morphology (short and squat rods versus elongated rods of isolates 10 and 13.2) and the lipase halo results (the lipase halos were significantly larger from isolate 9.2 indicating a more active lipase), it is likely that isolate 9.2 is a distinct *Pseudomonas* species than isolate 13.2.

While lipases are the most commonly identified plastic-degrading enzymes, the presence of a lipase is suggestive but generally not conclusive of whether an isolate is capable of degrading plastic. Additionally, there are many kinds of plastics which are not uniformly degraded by all lipases (see Yoshida S, et al. 2016. Science 351:1196-9). Therefore, it was important to directly test the ability of these environmental isolates to degrade plastic. Liquid cultures were set up with each lipase-positive consortium inoculated into carbon free media. This forces plastic to be used as a carbon source rather than other nutrients in the media. A sterilized pre-weighed plastic strip of low-density polyethylene (LDPE), high-density polyethylene (HDPE), or PET was placed into each tube. Additionally, previous studies have shown that UV pre-treatment, which more accurately mimics the environmental exposures seen in landfill and ocean plastic patches, can enhance plastic degradation via the introduction of lipase-cleavable ester bonds. These experiments were set up with lipase positive consortia (consortia 9, 10, and 13). Samples must incubate for at least 6 weeks, if not much longer, in order to see any appreciable change and so some experiments were set up prior to isolation of individual members of each consortium. Incubations took place at 26° C. for six weeks.

Figure 5:
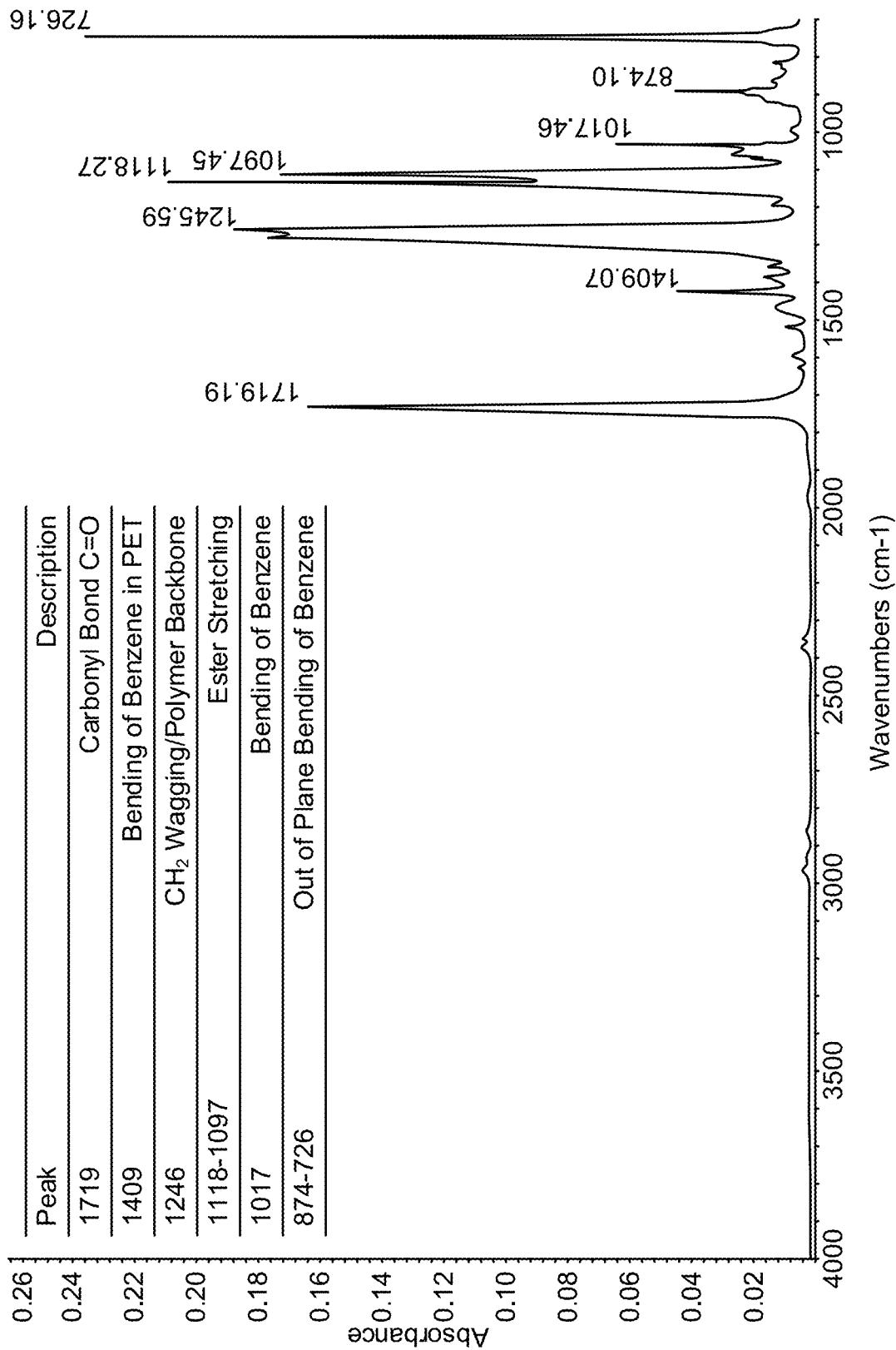
FIG. 5 shows Fourier-transform infrared spectroscopy (FTIR) analysis of virgin PET. Peaks are described according to bond identities. Degradation is assessed by comparing the intensity of the carbonyl peak (1719 $cm^{-1}$) to the benzene peak at 1409 $cm^{-1}$.

Fourier-transform infrared spectroscopy (FTIR) was used to assess breakdown of PET plastic at the bond level. FTIR spectra were captured for virgin PET and plastic strips incubated with each lipase positive consortium. A spectrum of virgin PET is shown in FIG. 5 with important peaks identified corresponding to various bonds inherent to PET.

The biodegradation of plastic is assessed by comparing the relative intensities of the carbonyl peak (1719 cm$^{-1}$) to another peak within the spectrum—in this case the peak at 1409 cm$^{-1}$ corresponding to the bending of the benzene ring—in a ratio termed the carbonyl index.

Decreases in the carbonyl index are indicative of plastic degradation as carbonyl bonds are lost due to cleavage and release of short hydrocarbon chains. These hydrocarbon chains, if small enough, are then able to be taken up by bacteria and used as a source of carbon and energy. Carbonyl indexes were calculated for PET with and without UV pretreatment incubated with the three consortia (Table 1). The carbonyl index of non-UV irradiated plastic did not decrease when incubated with consortium 9, consortium 13, or isolate 10. For PET pre-treated with UV, all three consortia/isolate showed a decrease in the carbonyl index, indicating degradation (Table 1). In addition, the Full Consortium, containing all three consortia/isolate, had the lowest carbonyl index of all samples, 3.35, compared to the blank, 4.2, which suggests that use of multiple lipase producers together may have a combined effect on plastic degradation. Overall, the decrease in the carbonyl index was greatest in the UV pre-treated samples, which indicates that UV treatment and microorganism biodegradation are synergistic.

TABLE 1

The calculated carbonyl ratio for each UV-irradiated and non-UV irradiated PET treatment condition following 6-week incubation in carbon-free media.

| Treatment Condition[1] | Average peak height (1719 cm$^{-1}$) | Average peak height (1409 cm$^{-1}$) | Average Carbonyl Index |
|---|---|---|---|
| Non-UV irradiated plastic | | | |
| Virgin[2] | 0.1155 | 0.025 | 4.62 |
| Blank[3] | 0.0512 | 0.0112 | 4.8 |
| Consortium 9 | 0.02 | 0.0037 | 5.0 |
| Isolate 10 | 0.0474 | 0.0103 | 4.6 |
| Consortium 13 | 0.0484 | 0.0094 | 6.0 |
| UV-irradiated plastic | | | |
| Virgin | 0.1632 | 0.0353 | 4.63 |
| Blank | 0.138 | 0.0322 | 4.2 |
| Consortium 9 | 0.0567 | 0.0146 | 3.88 |
| Isolate 10 | 0.0409 | 0.011 | 3.7 |
| Consortium 13 | 0.0734 | 0.0197 | 3.7 |
| Full Consortium | 0.1047 | 0.307 | 3.35 |

[1]Blank PET strips were incubated in carbon-free media with or without bacterial inoculate. All experiments were carried out in triplicate but due to equipment constraints of FTIR, single points were analyzed and are reflected in this table.
[2]Blank PET strips were incubated in carbon-free media with no bacterial inoculate. All experiments were carried out in triplicate but due to equipment constraints of FTIR, only single points were analyzed and are reflected in this table.
[3]Blank PET strips were incubated in carbon free media with no bacterial inoculate.

Given the evidence of plastic degradation by FTIR, the ability to form biofilms was assessed by SEM. Biofilms are the first, and one of the most important steps in assessing the ability to degrade plastic. Biofilm formation is essential for colonization of the plastic by microorganisms and without them, plastic cannot be degraded efficiently. There are multiple ways to assess biofilm formation but generally the most rigorous is via SEM. SEM allows for the visualization of bacterial colonization and biofilm architecture including extracellular polymeric substance (EPS) deposits which have been shown to be essential scaffolding for productive biofilms (see Ritenberg M, et al. 2016. ACS Chem Biol 11:1265-70). All three lipase-positive consortia were able to colonize and form biofilms on PET, to different extents (see FIG. 6). Consortium 13 had fewer adherent cells and less EPS deposits on the PET, indicating a reduced ability to form a biofilm on the plastic (see FIGS. 6A and 6B). Consortium 13 was the only consortium without evidence of pili, suggesting: 1) that these pili may be essential for robust biofilm formation and 2) that this *Pseudomonas* species may lack the genes necessary to form these pili, not allowing for robust biofilm formation (see FIG. 6D). Pili permit attachment to the plastic, and adherence between adjacent cells (solid white and dashed arrows in FIG. 6C, respectively), facilitating colony formation on hydrophobic plastic surfaces. The biofilm characteristics for each consortium are summarized in FIG. 6D. Despite the inability to form as mature of a biofilm on PET as consortium 9 and isolate 10, consortium 13 had consistently the lowest carbonyl index (Table 1), indicating a sufficient enough biofilm was formed in order to undergo plastic degradation.

Evidence of pili via SEM, in conjunction with the sequencing data identifying the isolates as *Pseudomonads*, suggests the *Pseudomonads* in consortium 9 and isolate 10 use the Type IV pili (TFP) system, as previously characterized, to lay down a biofilm and colonize the PET plastic. TFP have been identified as the only pili common to *Pseudomonas*, and in fact most Gram-negative bacteria have them (see Craig L, et al. 2004. Nat Rev Microbiol 2:363-78). TFP are spindly, fibrous organelles found on the surface of many gram-negative bacteria, including Pseudomonad species. They are generally involved in bacterial movement on solid surfaces through a twitching motility, as well as bacterial attachment to host cells and extracellular or environmental surfaces (see Wall D, et al. 1999. Mol Microbiol 32:1-10). Additionally, TFP have been shown to be involved in the uptake of macromolecules, as demonstrated by its role in transforming DNA into *Neisseria gonorrhoeae* bacterial cells (see Wolfgang M, et al. 1998. Mol Microbiol 29:321-30). TFPs have been shown to be an essential component for bacterial biofilm formation, as evidenced by TFP knockout *Pseudomonas aeruginosa*'s failure to build up multi-cell layers of biofilm on a solid surface (see Smyth C J, et al. 1996. FEMS Immunol Med Microbiol 16:127-39 and Merz A J, et al. 1999. Mol Microbiol 32:1316-32). Here, the TFP appear to be responsible for laying down islands of EPS, as observed with SEM, and bacteria can be found embedded in these rudimentary biofilms (see FIG. 6B).

Pili were not observed in SEM imaging of consortium 13, though it was identified as a Pseudomonad by 16S sequencing. This could be explained because not all *Pseudomonads* have a TFP system. In fact, *Pseudomonas putida*, a related species, lacks all the necessary subunits to make functional pili and have been observed to have none on their surface (see de Groot A, et al. 1994. J Bacteriol 176:642-50). This lack of functional TFP could explain why consortium 13, which contained one lipase producer and one gram positive rod, struggled to colonize PET. The number of bacteria adherent to the surface of the PET was minimal and the EPS production was the least, as observed by SEM.

Aiding colonization through the addition of biosurfactants could also assist in creating initial biofilms. Biosurfactants have been shown to both promote and antagonize biofilm formation by allowing for initial colony formation and maintaining nutrient channels essential for a productive mature biofilm, and then promoting their dissolution once migration is necessary (see Pamp S J, et al. 2007. J Bacteriol 189:2531-9 and Banat I M, et al. 2014. Appl Microbiol Biotechnol 98:9915-29). Biosurfactants have the added benefit of increasing hydrophobic surface area to not only aid in the attachment of bacteria, but also to enhance polymer solubility throughout the degradation process (see Chang J S, et al. 2004. Environ Toxicol Chem 23:2816-22 and Santos D K, et al. 2016. Int J Mol Sci 17:401). Synthetic biosurfactants like mineral oil can also aid in the colonization and degradation of plastic (see Gilan (Orr) I., et al. 2004. Applied Microbiology and Biotechnology 65:97-104).

Surfactants are compounds that reduce surface and interfacial tension at the interfaces between solids, liquids, and gasses, allowing such compounds to mix and disperse (see ref. 1). The majority of synthetic surfactants are petroleum based, and usually non-biodegradable and harmful to the environment. However, the synthetic surfactant mineral oil has been shown to enhance microbial degradation of polyethylene plastic by *Rhodococcus ruber* (see ref. 2). Biosurfactants are low molecular weight (<10 kDa) glycolipid and lipopeptide compounds that are synthesized and secreted by a wide variety of bacterial organisms. Biosurfactants significantly reduce the interfacial surface tension of hydrocarbon compounds, which aids bacterial colonization and degradation (see refs. 3 and 4). Biosurfactants are produced by bacteria naturally, but their production has been shown to be induced or increased under certain stressful conditions. For example, *Rhodococcus erythropolis* DSM43215 produced large quantities of a trehalose lipids when incubated with n-alkanes hydrocarbons (see ref. 3). Exemplary biosurfactants that can be produced by certain bacteria are provided in Table 2 below.

3. Kretschmer A B H, Wagner F. 1982. Chemical and physical characterization of interfacial-active lipids from *Rhodococcus erythropolis* grown on n-alkanes. Applied and Environmental Microbiology 44:864-870.
4. Franzetti A G, I., Bestetti, G., Smyth, T. J. P., Banat, I. M. 2010. Production and applications of trehalose lipid biosurfactants. European Journal of Lipid Science and Technology 112:617-627.
5. Itoh S. S T. 1972. Effect of rhamnolipids on growth of *Pseudomonas auruginosa* mutant deficient in n-paraffin utilizing ability. Agricultural Biological Chemistry 36:2233-2235.
6. Spencer J. F. T SDM, Tulloch A. P. 1979. Extracellular glycolipids of yeasts. Economic Microbiology 3:523-524.
7. Alsohim A S, Taylor T B, Barrett G A, Gallie J, Zhang X X, Altamirano-Junqueira A E, Johnson L J, Rainey P B, Jackson R W. 2014. The biosurfactant viscosin produced by *Pseudomonas fluorescens* SBW25 aids spreading motility and plant growth promotion. Environ Microbiol 16:2267-81.
8. Ron E Z, Rosenberg E. 2001. Natural roles of biosurfactants. Environ Microbiol 3:229-36.
9. Fonseca de Faria A, Teodoro-Martinez, D., Nazareno de Oliveira Barbosa, G., Gontijo Vaz, B., Serrano Silva, I., Garcia, J., Tótola, M., Eberlin, M. N., Grossman, M., Alves, O., Durrant L. R. 2011. Production and structural characterization of surfactin (C14/Leu7) produced by *Bacillus subtilis* isolate LSFM-05 grown on raw glycerol from the biodiesel industry. Process Biochemistry 46:1951-1957.

TABLE 2

Relevant biosurfactants based on their producing organism and chemical nature

| Biosurfactant | Associated Genus/Species (reference) |
|---|---|
| 1. Glycolipids | a. *Rhodococcus erythropolis, Nocardia erythropolis, Arthrobacter* sp., *Mycobacterium* sp. (ref. 3) |
|   a. Trehalose lipids | |
|   b. Trehalose dimycolates | |
|   c. Trehalose dicorynomycolates | b. *Mycobacterium* sp., *Nocardia* sp. (see refs. 3 and 4) |
|   d. Rhamnolipids | |
|   e. Sophorolipids | c. *Arthrobacter* sp., *Corynebacterium* sp. (see ref. 4) |
| | d. *Pseudomonas aeruginosa, Pseudomonas* sp. (see ref. 5) |
| | e. *Candida* sp., *Torulopsis* sp. (see ref. 6) |
| 2. Lipopeptides and lipoproteins | a. *Bacillus licheniformis* |
|   a. Peptide-lipid | b. *Pseudomonas fluorescens* (see ref. 7) |
|   b. Viscosin | c. *Bacillus subtilis* (see refs. 4, 8, and 9) |
|   c. Surfactin | d. *Serratia marcescens* (see ref. 10) |
|   d. Serrawettin | e. *Arthrobacter* sp. (see ref. 11) |
|   e. Arthrofactin | f. *Bacillus subtilis* (see ref. 12) |
|   f. Subtilisin | g. *Myroides* sp., *Pseudomonas* sp., *Agrobacterium* sp., *Gluconobacter* sp. (see refs. 13-15) |
|   g. Ornithine lipids | |
| 3. Polymeric Surfactants | a. *Arethrobacter calcoaceticus* (see ref. 16) |
|   a. Emulsan | |
|   b. Biodispersan | b. *Arethrobacter calcoaceticus* (see ref. 17) |
|   c. Liposan | c. *Candida lipolytica* (see ref. 18) |

BIOSURFACTANT REFERENCES

1. Banat I M, Makkar R S, Cameotra S S. 2000. Potential commercial applications of microbial surfactants. Appl Microbiol Biotechnol 53:495-508.
2. Gilan H, Y., Sivan, A. 2004. Colonization, biofilm formation and biodegradation of polyethylene by a strain of *Rhodococcus ruber*. Applied Microbiology and Biotechnology 65.

10. Li H, Tanikawa T, Sato Y, Nakagawa Y, Matsuyama T. 2005. *Serratia marcescens* gene required for surfactant serrawettin W1 production encodes putative aminolipid synthetase belonging to nonribosomal peptide synthetase family. Microbiol Immunol 49:303-10.
11. Morikawa M, Daido H, Takao T, Murata S, Shimonishi Y, Imanaka T. 1993. A new lipopeptide biosurfactant produced by *Arthrobacter* sp. strain MIS38. J Bacteriol 175:6459-66.

12. Kamal M, Hoog J O, Kaiser R, Shafqat J, Razzaki T, Zaidi Z H, Jornvall H. 1995. Isolation, characterization and structure of subtilisin from a thermostable *Bacillus subtilis* isolate. FEBS Lett 374:363-6.
13. Maneerat S, Bamba T, Harada K, Kobayashi A, Yamada H, Kawai F. 2006. A novel crude oil emulsifier excreted in the culture supernatant of a marine bacterium, Myroides sp. strain SM1. Appl Microbiol Biotechnol 70:254-9.
14. Kawai Y, Yano, I., Kaneda, K., Yabuuchi, E. 1988. Ornithine-containing lipids of some Psuedomonas species. European Journal of Biochemistry 175:633-641.
15. Tahara Y, Kameda M, Yamada Y, Kondo K. 1976. An ornithine-containing lipid isolated from *Gluconobacter cerinus*. Biochim Biophys Acta 450:225-30.
16. Shabtai Y, Gutnick D L. 1985. Exocellular esterase and emulsan release from the cell surface of *Acinetobacter calcoaceticus*. J Bacteriol 161:1176-81.
17. Markande A R. 2013. Studies on Ecophysiological Potential of Bioemulsifier Produced by *Bacillus* Species. Doctor of Philosophy Microbiology. The Maharaja Sayajirao University of Baroda, Gujurat, India.
18. Cirigliano M C, Carman G M. 1985. Purification and Characterization of Liposan, a Bioemulsifier from *Candida lipolytica*. Appl Environ Microbiol 50:846-50.

The contents of each of the Biosurfactant References noted above (references 1-18) are hereby incorporated by reference in their entirety.

Pretreatment of plastic with UV radiation has been shown to enhance biodegradation of plastics through free radical formation and introduction of ester bonds into the hydrocarbon backbone of plastic polymers (see Singh B S, et al. 2008. Polymer Degradation and Stability 93:561-584). Thirty-minute UV pretreatment was attempted here, but perhaps must be longer. While 30 minutes is within range for a cellular survival study, some biodegradation studies have exposed plastic polymers to UV for up to eight weeks at 365 nM (see Lee B, et al. 1991. Appl Environ Microbiol 57:678-85 and Yousif E, et al. 2013. Photodegradation and photostabilization of polymers, especially polystyrene: review. Springerplus 2:398). Nonetheless, the carbonyl index decreased, as a percentage, more in the 30-minute UV pretreated PET samples than the non-UV pretreated ones in this study. The second factor is shortened incubation times. Incubations in this study were six weeks, but some plastic degradation studies do six months or longer when assessing weight loss in particular (see Gomez E M J, F. 2013. Polymer Degradation and Stability 98:2583-2591 and Kyaw B M, et al. 2012. Indian J Microbiol 52:411-9).

Organic catalysts or biocatalysts may be used to initiate or facilitate the breakdown of PET and may also be useful in developing technology for efficient biodegradation by consortia bacteria, such as glycolysis, methanolysis, and hydrolysis reactions. Sunlight and physical abrasion may be used, though such methods may produce microplastics (e.g., less than 5 mm) that can be degraded by soil bacteria, though slowly over years. These plastic microparticles, however, pose danger to wildlife, ecosystems, and ultimately human health.

Organic catalysts or biocatalysts, such as 1,5,7-Triazabicyclo[4.4.0]dec-5-ene (TBD) can induce the glycolysis of PET, producing BHET. BHET may be completely degraded by the Full Consortium of bacteria in three weeks. 1H nuclear magnetic resonance can be used to assess depolymerization efficiency. Organic catalysts or biocatalysts have the advantage of not needing to introduce heavy metals into the system, not needing high temperature for catalyzing glycolysis or other mechanisms of breakdown, and they can be regenerated. In some embodiments, organic catalysts or biocatalysts that may be used for the initiation of the biodegradation of PET to form the more bioavailable compound BHET may be selected from 1,5,7-Triazabicyclo [4.4.0]dec-5-ene (TBD) (see Fukushima et al. 2001. Journal of Polymer Science Part A: Polymer Chemistry, 49(5):1273-1281), N-heterocyclic carbene (see Kamber et al. 2010. J. Chem. Educ. 87, 5, 519-521), and the like.

ADDITIONAL REFERENCES IN THE DEPOLYMERIZATION OF PET TO FORM BHET

Farahat, M. S.; Nikles, D. E. Macromol Mater Eng 2001, 286, 695-704
Vaidya, U. R.; Nadkarni, V. M. Ind Eng Chem Res 1987, 26, 194-198.
Shukla, S. R.; Harad, A. M.; Jawale, L. S. Waste Manage 2008, 28, 51-56.
Halacheva, N.; Novakov, P. Polymer 1995, 36, 867-874
Pardal, F.; Tersac, G. Polym Degrad Stab 2006, 91, 2567-2578.
Chen, C. H.; Chen, C. Y.; Lo, U. W.; Mao, C. F.; Liao, W. T. J Appl Polym Sci 2001, 80, 943-948.
Baliga, S.; Wong, W. T. J Polym Sci Part A: Polym Chem 1989, 27, 2071-2082.

Figure 11:
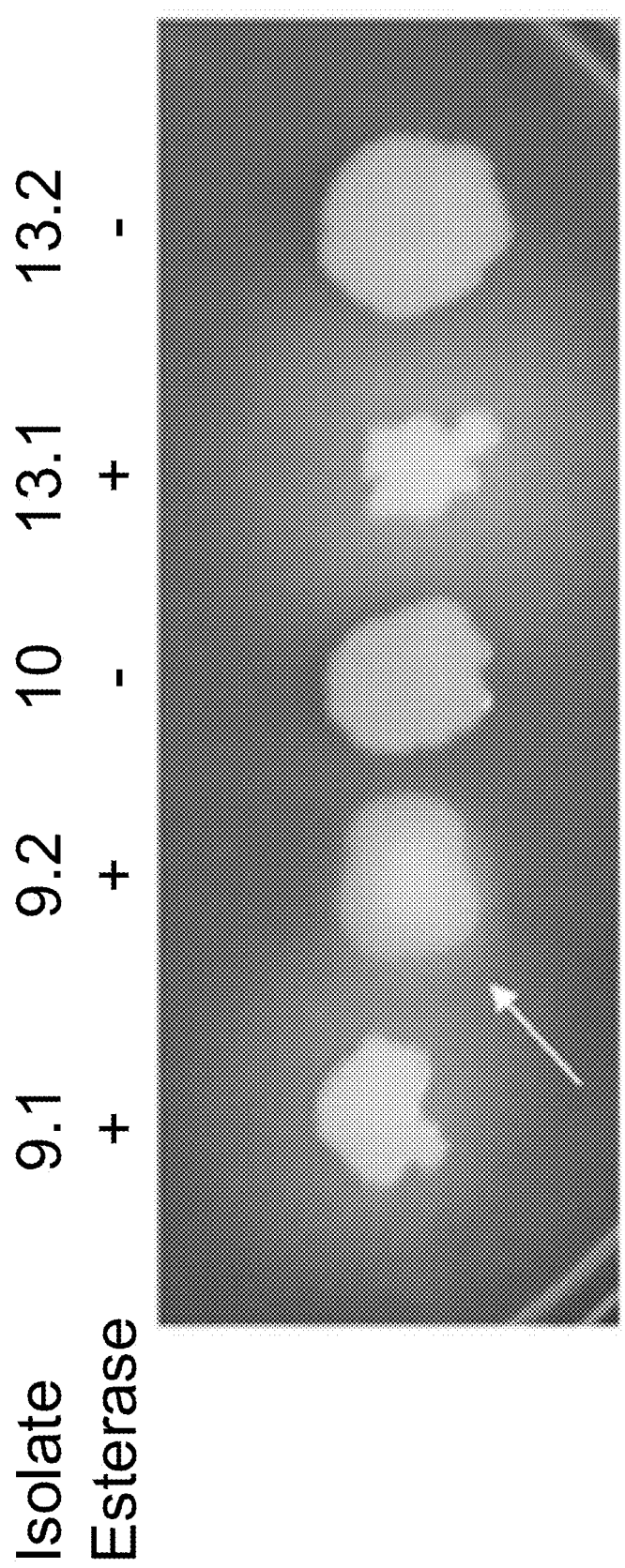
FIG. 11 shows the screening of individual isolates for non-specific esterase activity. Isolates 9.1 (*Bacillus thuringiensis* str. C15), 9.2 (*Pseudomonas* sp. B1), 10 (*Pseudomonas* sp. SWI36), 13.1 (*Bacillus albus* str. PFYN01) and 13.2 (*Pseudomonas* sp. SWI36) were grown on $CaCl_2$-Tween 20 agar to screen for esterase activity. Isolates were incubated at 26° C. for 96 hrs. Precipitant appears when esterases are secreted beyond the colony growth for all isolates except 10 and 13.2. The white arrow points to precipitant observed for isolate 9.2.

The consortia members produce both lipase and esterase activity. Lipases function at hydrophobic surfaces, while esterases cleave ester bonds at the hydrophilic interface at the termini of PET polymers (see Chahiniana and Sarda 2009. Protein Peptide Letters 16(10):1149-61). Non-specific esterase activity was identified by plating the isolates on solid medium containing $CaCl_2$-Tween 20 and screening for calcium salt precipitation. Isolates 9.1, 9.2, and 13.1 all exhibited secreted esterase activity (see FIG. 11). Previously, carboxylesterase of a *Bacillus* sp. was shown to partially hydrolyze PET polymers (see Wei and Zimmermann 2017. Microbial Biotechnology (10(6):1308-1322). Therefore, both lipases and esterases can be useful in degrading post-consumer PET plastic.

ESTERASES REFERENCES

H. Chahiniana and L. Sarda. Distinction Between Esterases and Lipases: Comparative Biochemical Properties of Sequence-Related Carboxylesterases, Protein Peptide Letters 16(10):1149-61 September 2009.
Ren Wei and Wolfgang Zimmermann. Microbial enzymes for the recycling of recalcitrant petroleum-based plastics: how far are we? Microbial Biotechnology, 10(6):1308-1322, March 2017.

In some embodiments, various bacterial species with different strengths may be combined that can work in concert to enhance, improve, and/or maximize polymer degradation. For example, the data presented herein suggests that the Pseudomonad in consortium 13 (isolate 13.2) is a powerful plastic degrader, but it appears to have less ability to form a healthy and mature biofilm compared to consortium 9 and isolate 10 (see FIG. 6B). This may limit its ability to degrade plastic and maximize its full plastic-degrading potential. However, incubating isolate 13.2 with another species that are capable of robust biofilm formation, such as the Pseudomonad in consortium 9, may allow for the formation of a complex biofilm that can be utilized by isolate 13.2, perhaps increasing plastic degradation potential.

In some embodiments, a bioaugmentation method may include growing plastic-degrading consortia of bacteria within a contained, carbon-free system. Growing the bacteria in a carbon-free system may ensure that the bacteria utilize and degrade plastic waste that is introduced into the system (e.g., as a carbon source). Pre-treatment of plastic can take place prior to bacterial degradation to render the inert plastic or polymer more amenable to bacterial degradation. Plastic waste may first be subjected to UV pretreatment(s) to introduce functional groups into the inert polymer backbone that are more easily recognized and cleavable by bacterial lipases. UV pretreatment(s) may be followed by mechanical grinding or disintegration of plastic waste (e.g., into smaller fragments), which can result in increased surface area for bacterial colonization. The plastic waste may then be fed into the contained system to be degraded. In certain embodiments, end products from the process may include bacterial biomass and carbon dioxide. The biomass may be used as a fertilizer. The carbon dioxide generation may be offset by the introduction of carbon-fixing bacteria into the system. Alternatively, the carbon dioxide generation may be offset by disposing the system in plant-rich area.

A first aspect of the disclosure relates to a method of degrading a polymer. The method can include incubating the polymer with one or more *Pseudomonads* and/or *Bacillus* species.

In some embodiments, the one or more *Pseudomonads* may be *Pseudomonas* sp. SWI36 and/or *Pseudomonas* sp. B10. For example, the one or more *Pseudomonads* may be selected from at least one of isolate 9.2 deposited as NRRL No. B-67633, isolate 10 deposited as NRRL No. B-67630, and/or isolate 13.2 deposited as NRRL No. B-67634. In certain embodiments, the *Bacillus* species may be *Bacillus thuringiensis* str. C15 and/or *Bacillus albus* str. PFYN1. For example, the one or more *Bacillus* species may be selected from at least one of isolate 9.1 deposited as NRRL No. B-67632 and/or isolate 13.1 deposited as NRRL No. B-67631. NRRL refers to the Agricultural Research Service (ARS) Culture Collection International Depositary Authority, located at 1815 N. University Street, Peoria, Illinois 61604. Isolates 9.1, 9.2, 10, 13.1, and 13.2 were each deposited with ARS on Jun. 1, 2018 under the terms of the Budapest Treaty.

The polymer may be selected from at least one of a PET, an HDPE, an LDPE, and/or a polypropylene (PP). In some embodiments, the polymer can be a PET. In certain embodiments, the polymer can be an HDPE. In various embodiments, the polymer can be an LDPE. In further embodiments, the polymer can be a PP.

The polymer and the one or more *Pseudomonads* and/or *Bacillus* species may be incubated in a liquid carbon-free basal medium (LCFBM). In some embodiments, the method of degrading the polymer may include exposing the polymer to UV radiation. For example, the polymer may be exposed to UV radiation prior to incubating the polymer with the one or more *Pseudomonads* and/or *Bacillus* species. The polymer may be exposed to UV radiation for between about 15 minutes and about 10 hours, between about 30 minutes and about 5 hours, between about 1 hour and about 3 hours, or another suitable period of time.

In certain embodiments, the method may further include incubating the polymer and the one or more *Pseudomonads* and/or *Bacillus* species with a biosurfactant. In various embodiments, the biosurfactant may be generated by the one or more *Pseudomonads* and/or *Bacillus* species. In some embodiments, the biosurfactant may be added to the incubation. The biosurfactant may be selected from at least one of mineral oil, trehalose lipid (e.g., trehalose dimycolate, trehalose dicorynomycolate, etc.), rhamnolipid, sophorolipid, peptide-lipid, viscosin, surfactin, serrawettin, arthrofactin, subtilisin, ornithine lipid, emulsan, biodispersan, liposan, and/or another suitable biosurfactant.

In certain embodiments, the method may further include incubating the polymer and the one or more *Pseudomonads* and/or *Bacillus* species with an organic catalyst or a biocatalyst. In some embodiments, the organic catalyst or biocatalyst may be added to the incubation. The organic catalyst or biocatalyst may be selected from at least one of 1,5,7-Triazabicyclo[4.4.0]dec-5-ene (TBD), N-heterocyclic carbene, and/or another suitable organic catalyst or biocatalyst.

The method may further include breaking, cutting, disintegrating, and/or grinding the polymer. For example, the polymer may be ground prior to incubating the polymer with the one or more *Pseudomonads* or *Bacillus* species.

Another aspect of the disclosure relates to a kit for degrading a polymer. The kit may include one or more *Pseudomonads* and/or *Bacillus* species. The kit may also include an incubator for culturing the one or more *Pseudomonads* and/or *Bacillus* species. The one or more *Pseudomonads* may be *Pseudomonas* sp. SWI36 and/or *Pseudomonas* sp. B10. For example, the one or more *Pseudomonads* may be selected from at least one of isolate 9.2 deposited as NRRL No. B-67633, isolate 10 deposited as NRRL No. B-67630, and/or isolate 13.2 deposited as NRRL No. B-67634. In certain embodiments, the *Bacillus* species may be *Bacillus thuringiensis* str. C15 and/or *Bacillus albus* str. PFYN01. For example, the *Bacillus* species may be selected from at least one of isolate 9.1 deposited as NRRL No. B-67632 and/or isolate 13.1 deposited as NRRL No. B-67631.

Another aspect of the disclosure relates to a method for degrading a polymer-containing substrate. The method may include obtaining a polymer-containing substrate (e.g., a PET substrate, an HDPE substrate, an LDPE substrate, and/or a PP substrate). In some embodiments, the method may include breaking, cutting, disintegrating, and/or grinding at least a portion of the polymer-containing substrate. For example, the method may include mechanically breaking, cutting, disintegrating, and/or grinding at least a portion of the polymer-containing substrate. In certain embodiments, the method may include subjecting the polymer-containing substrate to UV radiation. In various embodiments, the method may include incubating the polymer-containing substrate with one or more *Pseudomonads* and/or *Bacillus* species.

Another aspect of the disclosure relates to a composition for degrading a polymer-containing substrate, wherein the composition may include one or more *Pseudomonads* and/or *Bacillus* species as described above.

Another aspect of the disclosure relates to a composition for degrading a polymer-containing substrate, wherein the composition may include one or more *Pseudomonads* wherein the one or more *Pseudomonads* may be selected from at least one of isolate 9.2 deposited as NRRL No. B-67633, isolate 10 deposited as NRRL No. B-67630, and/or isolate 13.2 deposited as NRRL No. B-67634.

Yet another aspect of the disclosure relates to a composition for degrading a polymer-containing substrate, wherein the composition may include a *Bacillus* species, wherein the *Bacillus* species may be selected from at least one of isolate 9.1 deposited as NRRL No. B-67632 and/or isolate 13.1 deposited as NRRL No. B-67631.

EXAMPLES

The following examples are illustrative of disclosed methods and compositions. In light of this disclosure, those of skill in the art will recognize that variations of these examples and other examples of the disclosed methods and compositions would be possible without undue experimentation.

Example 1—Soil Sample Collection

Soil samples (500 g) were collected from eight different sites in Southeast Texas. Sample 1 was collected at the Jones Road Chemical Plume Superfund Site at 1160 Jones Road, Houston, TX. Sample 2 was collected at the Baer Road Foundry Superfund Site in $5^{th}$ Ward, Houston, TX. Sample 3 was collected outside of the gates of the Pasadena Refining System at 111 Red Bluff Road. Sample 4 was collected in the parking lot of the Pasadena Refining System at 111 Red Bluff Road, Pasadena, TX. Sample 5 was collected adjacent to the main gas pipeline at the Pasadena Refining System. Sample 6 was collected at the Baer Road Power Station in Houston, TX. Sample 7, was collected six inches beneath the surface at East Beach, Galveston, TX, roughly 12 yards from the shoreline. Sample 8 was collected from the topsoil outside of the transformers of the West Park Power Station, Houston, TX. All samples were collected roughly six inches beneath the topsoil layer and immediately refrigerated before being transported to Portland, OR in sealed re-sealable zipper storage bags.

Example 2—Bacterial Extraction from Soil

Each soil sample (2 g) was resuspended in 9 mL phosphate buffered saline (PBS) prepared accordingly per 1 liter $diH_2O$: 8 g NaCl, 0.2 g KCl, 1.44 g $Na_2HPO_4$, and 0.24 g $KH_2PO_4$ adjusted to pH 7.4 using a pH meter and autoclaved for 20 minutes at 15 psi, 121° C. The soil and PBS suspensions were placed on a rotary shaker (250 rpm) for 24 hours. The sediment was allowed to settle, and 100 µL of this suspension was then spread on LB agar plates prepared accordingly per 1 liter $diH_2O$: 10 g tryptone, 5 g yeast, 5 g NaCl, 18 g agar adjusted to pH 7 using a pH meter, autoclaved at 15 psi, 121° C. Plates were inverted and incubated at 26° C. for 24 hours.

Example 3—Rhodamine Blue Agar

Rhodamine blue agar plates were prepared to test isolated bacterial colonies for lipase activity. Rhodamine agar plates were prepared accordingly per 1 liter: 950 mL $diH_2O$, 4.5 g nutrient broth powder, 1.25 g yeast extract, and 10 g agar. For the lipid emulsion media, 250 µL of TWEEN® 80 was added to 50 mL $diH_2O$ and emulsified in a blender. Olive oil (30 mL) was added to the lipoidal emulsion and blended until emulsified. The final lipoidal emulsion was adjusted to pH 7 using a pH meter. The base media and lipoidal emulsion were autoclaved separately. Following autoclaving, 20 mL of rhodamine blue (50 mg to 50 mL $diH_2O$ and filter sterilized) was added to sterile lipoidal emulsion. Lipoidal emulsion (50 mL) was then added to the base nutrient media to a final volume of 1 L and mixed thoroughly. Plates were poured in 12 mL volumes as described previously (Kouker G, et al. 1987. Appl Environ Microbiol 53:211-3). Colonies producing lipase on rhodamine blue plates are fluorescent when exposed to a 350-400 nm UV lamp. Olive oil is a lipase-specific long chain fatty acid that bacteria encoding a lipase can use as a source of carbon (see Lanka S L, et al. 2015. International Journal of Biological Chemistry 9:207-219). The hydrolysis and release of fatty acids bind to the dye rhodamine B, which causes a fluorescent halo to appear under 365 nm UV radiation exposure.

Example 4—Lipase Screening

Bacterial LB agar spread plates with 100 µL of liquid culture were screened for lipolytic activity via a colony lift assay from the LB spread plate to the rhodamine blue agar plates. A colony lift assay involves a large ceramic knob with the dimensions of a petri dish. Sterile felt is attached to the end of the knob, enabling the stamping of one group of bacterial colonies onto another plate. The rhodamine blue plates were inverted and incubated for 24 hours at 26° C. Lipase activity was then determined with a UV trans-illuminator at 365 nm. E. coli MC4100 was used as a negative control. Colonies and areas of growth that displayed glowing fluorescent halos were marked and re-streaked onto individual LB plates for isolation and purification. The eight soil samples were screened multiple times for any microbes with lipolytic activity. This assay was used throughout these experiments to ensure isolated strains remained lipase positive, particularly during attempts to purify mixed cultures.

Example 5—Purifying Cultures

Overnight cultures were grown of the three bacterial consortia and continuously re-streaked using the quadrant streak method on LB until pure cultures were obtained. Gram staining was utilized to help confirm bacterial strain purity and to corroborate 16S PCR results.

Example 6—Gram Staining

One sterile loop of liquid culture ($OD_{600}$=1.0) was spread onto sterile glass slides and flame fixed. The slide was flooded with crystal violet for one minute, washed with diH2O for five seconds, flooded with Gram's iodine for one minute, washed with diH2O for five seconds, flooded with 95% EtOH for ten seconds and flooded with safranin for one minute, prior to a final diH2O rinse and blotting with bibulous paper. Slides were visualized using 1000× magnification. Images were captured using a KEYENCE™ BZ-X700 inverted fluorescence and color microscope.

Example 7—LCFBM Supplemented with Plastic

Carbon free base media was prepared accordingly per 1 L of $diH_2O$: 0.7 g $KH_2PO_4$, 0.7 g $K_2HPO_4$, 1.0 g $NH_4NO_3$, and 0.005 g NaCl. A carbon free base media was prepared in order to ensure that the added plastic strips would be the sole source of carbon available to bacteria during the incubation. A 1 M stock solution of essential metals was prepared separately. In 100 mL of sterile $H_2O$: 7 g $MgSO_4*7H_2O$, 20 mg $Fe_2SO_4*7H_2O$, 20 mg $ZnSO_4*7H_2O$, and 9 mg $MnSO_4*H_2O$. This 1 M solution was stirred for four hours and 10 mL were filter sterilized and added to 1 L of autoclaved liquid base media. LDPE, HDPE, and PET samples were cut into 2.5 cm×0.5 cm strips. The strips were sterilized in 70% EtOH and hung in a biosafety cabinet to dry.

Cultures of the three lipase positive consortia were grown overnight in LB and diluted to an $OD_{600}$ of 1. This dilution ensured that an equal amount of bacteria was added to each sample. For single point LCFBM incubations, 10 µL of overnight culture was added to each 4 mL tube of LCFBM. Previously weighed and sterilized plastic strips were added to each tube (1 type per tube). The samples were incubated on a rotary shaker (26° C., 125 rpm) for three months. Samples were replenished with sterile LCFBM each month due to evaporation.

Following this experiment, another set of LCFBM cultures was set up under two treatment conditions: 1) UV pretreatment and 2) non-UV pretreatment. UV treated HDPE, LDPE, and PET strips (2.5 cm×0.5 cm) were exposed to 365 nm UV light for 30 minutes prior to sterilization and inoculation. The non-UV treated strips were also sterilized with EtOH prior to being added to test tubes. The non-UV treatment was included to test if UV pretreatment resulted in greater degradation. Each test tube was filled with 8 mL LCFBM and inoculated with 50 µL overnight culture ($OD_{600}$). Tubes were set up in triplicate and set up for static incubation at 26° C. Without being bound by any one particular theory, this was done to increase biofilm formation. These incubations lasted about six weeks.

Example 8—16S rRNA Gene PCR and DNA Sequencing

Direct colony PCR was conducted using the three isolated strains that exhibited lipase activity. PCR was conducted using universal 16S primers (Table 3), and a custom thermocycler program (Table 4), and the products were imaged in a 1.2% agarose gel in TAE buffer run at 110 mV for 30 minutes.

TABLE 3

Universal 16S Primer Pairs

| F[1] | A18 | 5'-ACTCCTACGGGAGGCAGC-3' (SEQ ID NO: 1) | 55° C.[2] |
|---|---|---|---|
| F | A19 | 5'-GTGCCSGCMGCCGCGGTAA-3'[3] (SEQ ID NO: 2) | 55° C. |
| R | S17 | 5'-AAGGAGGTGATCCAGCC-3' (SEQ ID NO: 3) | 55° C. |
| R | S20 | 5'-AGGCCCGGGAACGTATTCAC-3' (SEQ ID NO: 4) | 55° C. |

[1]Primer pairs: SDBact0338aA18(Fwd)/SDBact1525aS17(Rvs) and SDBact0515aA19(Fwd)/SDBact1525aS17(Rev) (see Kroes IL, et al. 1999. PNAS 96).
[2]Suggested annealing temperature (id.)
[3]S denotes a strong hydrogen bond (a G or C), and M denotes a C or an A, according to the IUPAC nucleotide ambiguity code.

TABLE 4

| Thermocycler program used for 16S rRNA gene amplification | | |
|---|---|---|
| Step | ° C. | Time |
| 1. Hot Start | 95 | 30 seconds |
| 2. Denature | 95 | 30 seconds |
| 3. Anneal | 54 | 30 seconds |
| 4. Extend | 68 | 2 minutes |
| 5. Go to step 2 | | |
| 6. Final | 72 | 5 minutes |

PCR products were cleaned using a GENECLEAN® kit with GLASSMILK™ technology. Briefly, each sample was diluted 1:4 in the GLASSMILK™ NaI solution prior to vortexing and centrifuging at 12000 rpm for 30 seconds. The supernatant was discarded and the pellet was washed and repelleted twice. The pellet was eventually resuspended in 5 µL of sterile water. Each sample was diluted 1:1 and the concentration was determined using a NANODROP™ instrument.

Following PCR cleanup using the GENECLEAN® kit, each sample was diluted to 1-2 ng/µl and sent to ACGT™ for Sanger sequencing using forward and reverse primers to achieve paired-end sequencing data for each isolate.

Example 9—Genus Identification Based on 16S rDNA Sequencing Data

Following sequencing at ACGT™, sequences were aligned to each other using BIOEDIT™ 7.2.5 biological sequence alignment editor prior to alignment, chromatograms were checked to ensure quality sequences and the first ~25-30 nucleotides from each sequence were eliminated due to sequencing artifact. The reverse primer sequence was then reverse-complemented and the two sequences (forward and modified reverse) were aligned to each other using pairwise alignment with sliding ends. Gaps were inserted manually until maximum alignment had been achieved. No chimeric sequences were observed. Only the core sequence with 100% agreement (150-764 nucleotides) was used to determine genus identity. Genus identification was done using nucleotide BLAST® (BLASTn), and identity cutoffs were set to only those matching 100%. The 100% identity metric was employed due to the conserved nature of the 16S rRNA gene targeted by these primers. These conserved regions of the 16S rRNA gene can tolerate very few base pair changes and thus a single base pair may be the difference between two genera. Additionally, short sequence alignments require a higher cutoff due to limited sequence input.

Example 10—IR Spectroscopy

Plastic PET strips were submerged in 30 mL 2% SDS in diH2O, and placed on a rotary shaker for two hours (225 rpm, 37° C.) to remove biofilms. Samples were then air-dried and visualized via ATR-FTIR solid infrared spectroscopy to assess for signs of plastic degradation. As plastic degrades, additional ester bonds and carboxyl bonds are created in the polymer backbone. The appearance or alteration of these groups causes changes in the absorbance intensities at 1719 $cm^{-1}$ and 1409 $cm^{-1}$, and these changes can be measured through the calculation of the carbonyl index ratio. This carbonyl ratio was calculated by finding the absorbance height at 1719 $cm^{-1}$ and 1409 $cm^{-1}$, and then dividing 1719/1409. A ratio of peaks allows a quantitative comparison of changes in IR spectra, as ratios account for sample differences in IR such as sample thickness. Additionally, carboxylation of shortened hydrocarbon chains by photo-oxidation mark hydrocarbon chains that are ready to enter the β-oxidation cycle. These changes in polymer bonds indicating degradation can be measured through comparing the carbonyl index of virgin plastic and inoculated plastic pieces. A low carbonyl index, as well as the appearance of additional carbonyl and OH peaks can be used to determine whether bacteria were actively converting plastic into precursors for β-oxidation cycle or the TCA cycle.

Example 11—Scanning Electron Micrography

Plastic samples were soaked in 2% phosphate buffered glutaraldehyde for cell fixation. For post-fixation, samples were submerged in 2% osmium tetra-oxide in an ice bath for three hours. The samples were then dehydrated in graded EtOH (50, 75, and 100%) baths for 15 minutes each before undergoing critical point drying with $CO_2$. Dried samples were coated using a gold sputter coater (LEICA™ ACE600 coater) and were visualized on a scanning electron microscopy instrument (FEI HELIOS NANOLAB™ 660 DUAL-BEAM™ microscope) operating at an electron beam intensity of 2 kV.

Figure 7:
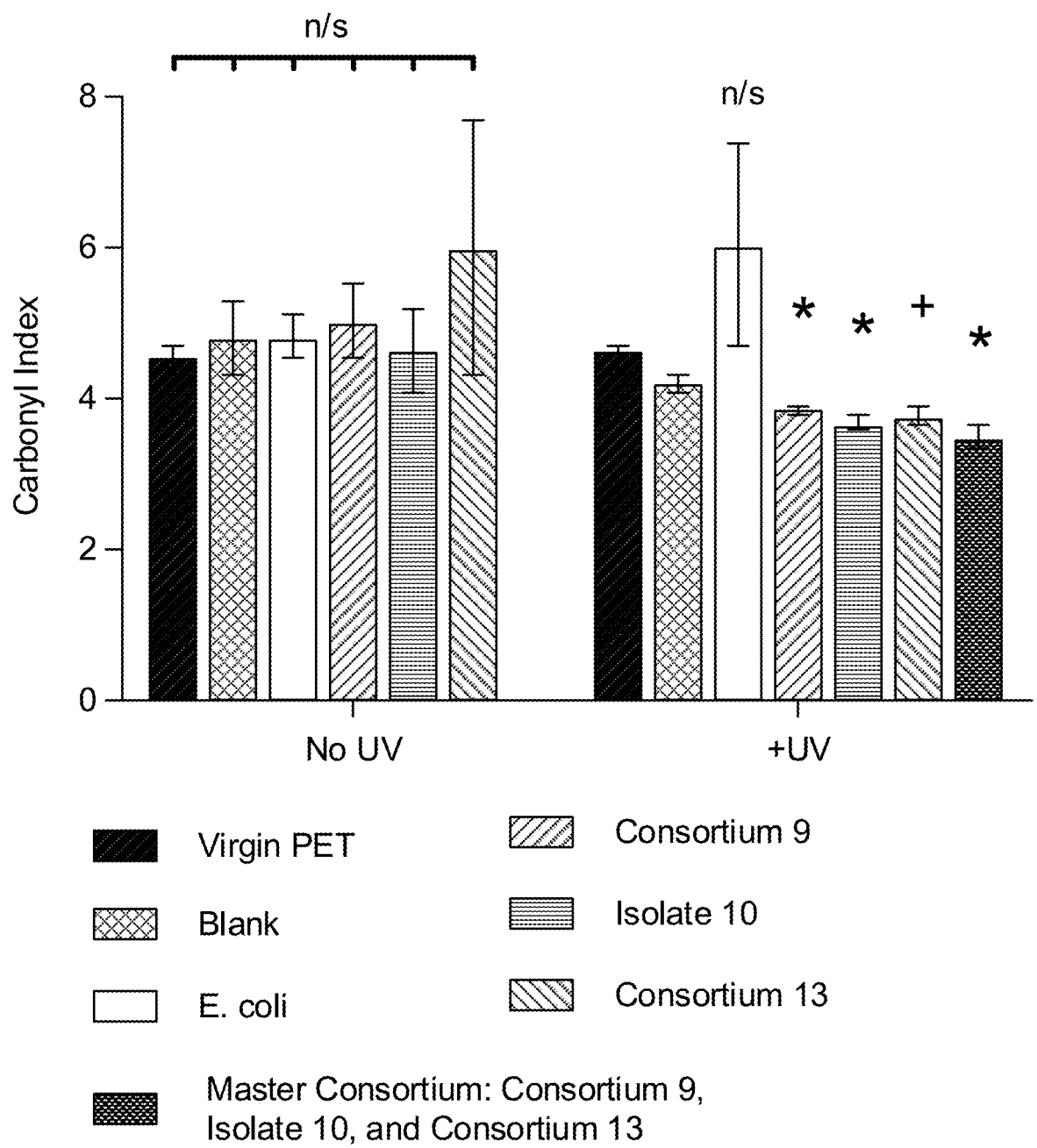
FIG. 7 depicts carbonyl index calculations for assessing degradation of PET using FTIR. *=p<0.05; +=p=0.0513; n/s=not significant. Statistics are comparing each sample to the respective "blank".

Example 12—Carbonyl Index Calculations for Assessing Degradation of PET Using FTIR Carbonyl indexes were calculated using the ester carbonyl peak at 1720 $cm^{-1}$ divided by the peak corresponding to the C—H stretching of benzene at 1409 $cm^{-1}$ (see FIG. 7). Each condition was performed in triplicate and each column represents the average±standard error of the mean. No incubations of PET alone were significantly degraded. UV-pretreated PET showed significant degradation when incubated with isolated consortia, but not control *E. coli*. *=p<0.05; +=p=0.058; n/s=not significant.

For each of the examples above, studies performed in biological triplicate or greater were compared via Student's t-test and a p-value of <0.05 was used to determine significance.

Example 13—Identification of Species in the Bacterial Consortia and Isolates

To identify the bacterial species in the bacterial consortia and isolates, 16S rRNA gene sequencing was performed for all five isolates (isolates 9.1, 9.2, 10, 13.1, and 13.2). Bacteria were grown in lysogeny broth at 26° C. overnight. DNA was extracted using the GenElute™ Bacterial Genomic DNA Kit (MilliporeSigma, St. Louis, MO). For library preparation, performed at the OSU Center for Genome Research and Biocomputing, Illumina's NexteraXT DNA Sample Prep Kit (Illumina, San Diego, CA) was used following the manufacturer's instructions. Sequencing was done on an Illumina MiSeq instrument, with run type of 150 bp paired end fragments on a Micro flow cell. The quality of the sequence fragments was assessed using FastQC (v0.11.5, 1) and Trimmomatic (v0.36, 2) for a quality standard of Q30 (LEADING:3 TRAILING:3 HEADCROP:10 SLIDINGWINDOW:4:30 MINLEN:36). High quality sequence fragments (1,652,364 read average per sample) were then assembled using SPAdes (v3.13.0, 3) with paired-end reads and also high-quality singletons. The quality and genome metrics were analyzed using Quast (v5). The draft genomes sizes range from 5,261,475 to 6,456,746 bps and the GC % content is 34.9 for the *Bacillus* draft genomes and 61.5 for the *Pseudomonas* draft genomes.

Assemblies were annotated using PROKKA (v1.13.3, 5). Close relatives of 16S rRNA genes were as follows: isolate 9.1 strain *Bacillus thuringiensis* str. C15 (100% coverage/100% identity), isolate 9.2 *Pseudomonas* sp. B10 (100% coverage/99% identity), isolate 10 *Pseudomonas* sp. SWI36 (100% coverage/100% identity), isolate 13.1 *Bacillus albus* str. PFYN01 (100% coverage/100% identity) and isolate 13.2 *Pseudomonas* sp. SWI36 (100% coverage/100% identity).

Figure 8:
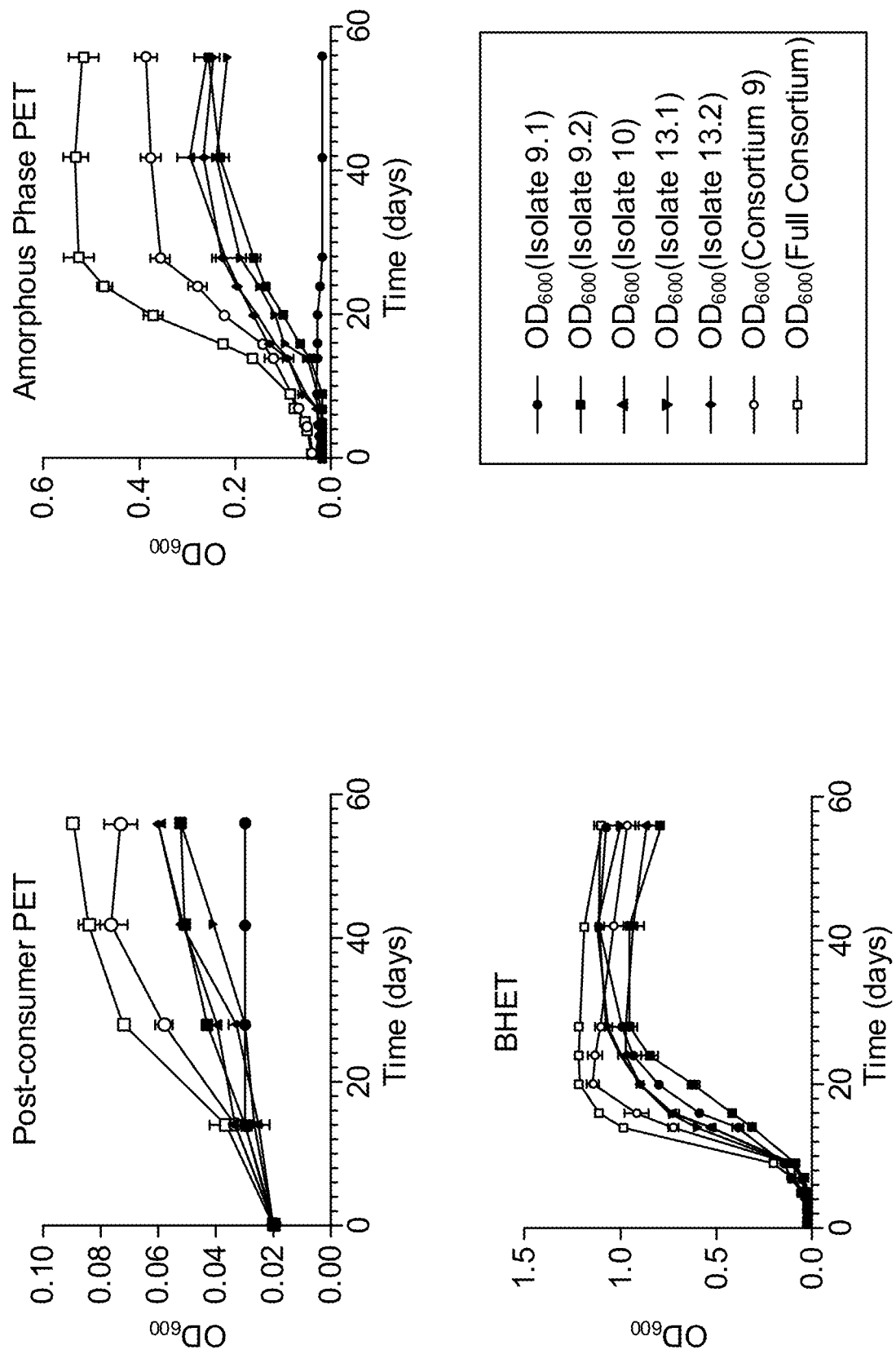
FIG. 8 is a series of graphs that illustrate consortium bacteria grow faster on PET and bis(2-hydroxyethyl)terephthalate (BHET) than individual isolates. Isolate 9.1 (*Bacillus thuringiensis* str. C15), isolate 9.2 (*Pseudomonas* sp. B10), a consortium of isolates 9.1 and 9.2 (*Bacillus thuringiensis* str. C15 and *Pseudomonas* sp. B10), isolate 10 (*Pseudomonas* sp. SWI36), isolate 13.1 (*Bacillus albus* str. PFYN01), isolate 13.2 (*Pseudomonas* sp. SW136), and a full consortium of all five isolates (isolates 9.1, 9.2, 10, 13.1, and 13.2) were given either 1 mM BHET, UV-treated amorphous phase PET pellets, or a UV-treated crystalline post-consumer PET strip as their sole carbon source. All consortia and isolates were grown overnight in LB and diluted to an $OD_{600}$ of 1 to ensure equal amounts of bacteria were added to all samples. Cultures were incubated at 30° C. with shaking at 200 rpm. Growth was measured every 2 weeks as the $OD_{600}$ and experiments were performed in triplicate. Error bars indicate standard error.

Example 14—Comparison of Consortia Bacteria and Individual Isolate Growth and Lipase Production on PET and BHET To determine the extent to which bacteria were able to grow on PET and BHET, individual isolates and consortia bacteria were inoculated as described in FIG. 8. Optical density measurements were taken over a 56-day period. It was consistently observed that consortia bacteria had lower doubling times and growth yield than individual isolates. This was observed for all three of the plastic products used as sole carbon sources in the carbon free medium. Doubling times for cultures containing the Full Consortium (9.1, 9.2, 10, 13.1 and 13.2) were 4.15, 2.63, and 1.16 days on crystalline PET, amorphous PET, and BHET, respectively. In addition, *Bacillus* isolate 9.1 was unable to grow on amorphous or crystalline PET in the absence of other consortia members, namely *Pseudomonas* isolate 9.2. *Bacillus* isolate 9.1 was unable to degrade the PET individually, and most likely lacked the enzymatic ability, lipases and/or esterases necessary to initially degrade PET into metabolizable products.

Because the consortia grew more robustly on plastic than individual isolates, it was predicted that the consortia bacteria would produce more lipase activity than the single isolates. Indeed, it was observed that Consortium 9, consisting of Isolates 9.1 and 9.2, had a greater halo to growth ratio on Rhodamine B plates than individual isolates 9.2 and 10 (Table 5).

TABLE 5

Ratios of Lipase Production to Colony Growth for Consortium 9 and Individual Isolates.

| Isolate | Least Square Mean Halo/Growth (n = 5) | Student's T Test Pairwise Comparison to 10 (Prob > \|t\|) | Student's T Test Pairwise Comparison to 9.2 (Prob > \|t\|) |
|---|---|---|---|
| 9.1 | 0 | <0.001* | <0.001* |
| 9.2 | 2.12 ± 0.04 | 0.0045* | — |
| 9.1 + 9.2 | 2.98 ± 0.04 | <0.001* | <0.001* |
| 10 | 2.30 ± 0.04 | — | 0.0045* |

*Bacillus thuringiensis* str. C15 with *Pseudomonas* sp. B10 (Consortium 9: Isolate 9.1 and Isolate 9.2), *Pseudomonas* sp. B10 (Isolate 9.2) alone and *Pseudomonas* sp. SWI36 (Isolate 10 or Isolate 13.2) alone were swabbed from PET plastic in cultures with PET as the sole carbon source, then inoculated onto Rhodamine B plates (n=5). The growth of each isolate and the corresponding halo diameters were measured after 48 hours. Diameters were quantified in ImageJ with a column average plot across each halo and the ratio of halo to growth was compared to the two *Pseudomonads* alone. As a control, by standard plate count, approximately equal numbers (~200 CFU/ml) of *B. thuringiensis* str. C15 and *Pseudomonas* sp. B10, constituting Consortium 9, were released from the PET plastic, upon gentle vortexing, after 8 weeks of incubation at room temperature. *B. thuringiensis* str. C15 (Isolate 9.1) alone was unable to grow using PET as a sole source of carbon.

Figures 9A, 9B:
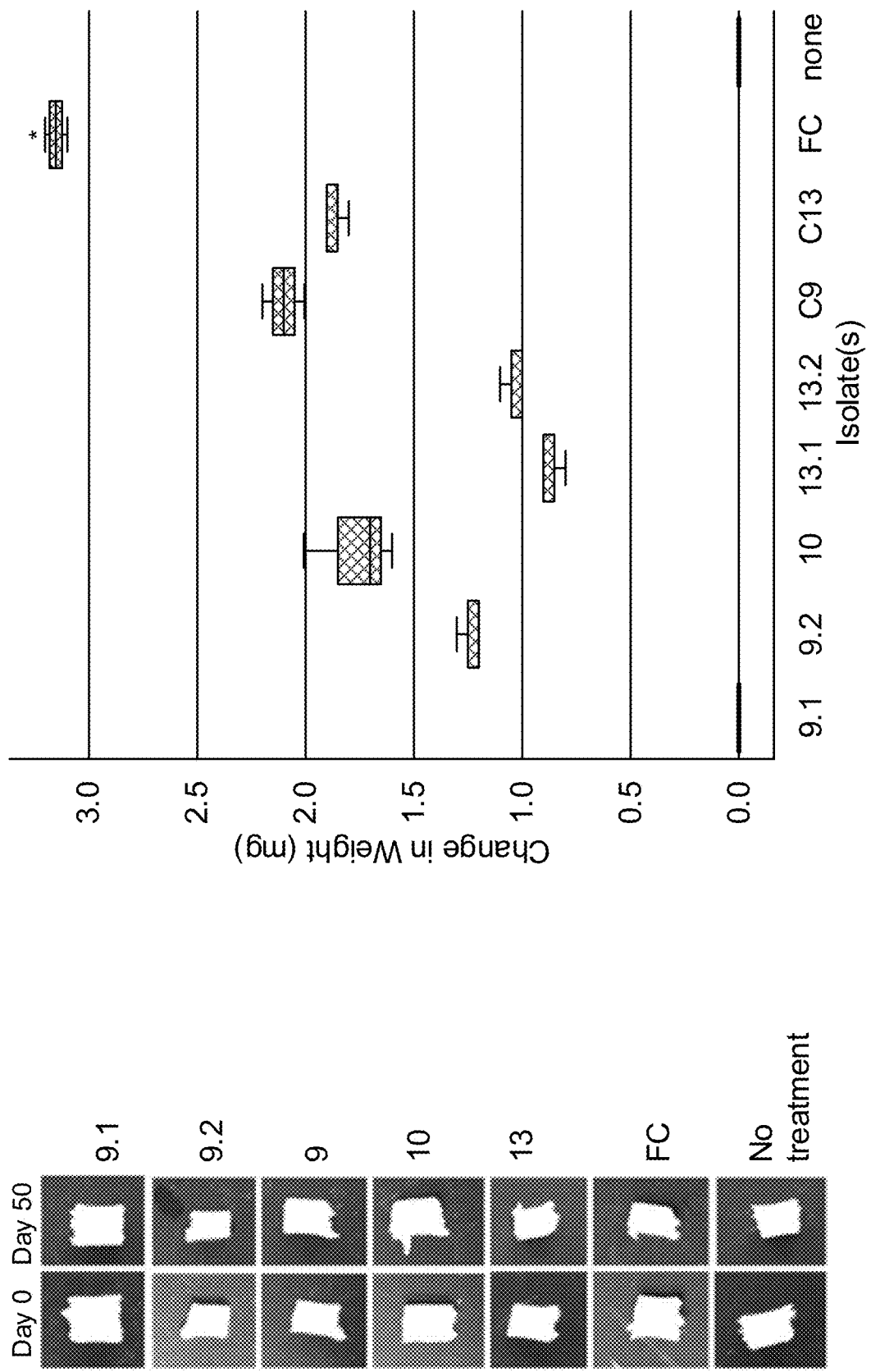
FIGS. 9A and 9B show that the full consortium (isolates 9.1, 9.2, and 10, 13.1, and 13.2) degrades PET to a greater extent than any individual isolate, or other consortia over a 50-day period. Granular PET (Sigma Aldrich, 1.68 g/mL at 25° C., melting point: 250-255° C.) was pre-treated overnight with UV radiation (250 nm). Cultures of individual isolates, consortium 9 (isolates 9.1 and 9.2), consortium 13 (isolates 13.1 and 13.2), and full consortium (FC; isolates 9.1, 9.2, 10, 13.1, and 13.2) were grown overnight in LB and diluted to an $OD_{600}$ of 1 to ensure equal amounts of bacteria were added to each sample. Aliquots of each overnight culture were washed with 1×PBS (2 times) and equal volumes of bacteria were added to the appropriate 10 mL tube of liquid carbon-free basal medium (LCFBM) with 0.1 g total PET (starting $OD_{600}$ 0.02). The samples were incubated at 30° C. without shaking for 6 weeks. A negative control with UV-treated granular PET in media without inoculation was kept under the same conditions.
Figure 10B:
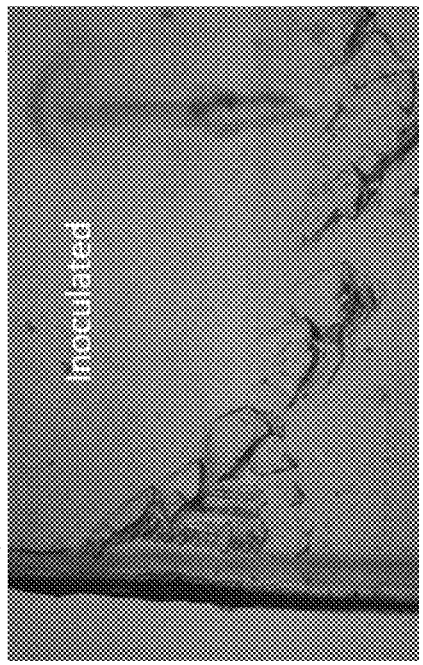
FIGS. 10A and 10B depict physical evidence of PET degradation in inoculated samples. The full consortium, consisting of all five bacterial consortia isolates (isolates 9.1, 9.2, 10, 13.1, and 13.2) were inoculated into carbon free medium containing post-consumer, crystalline PET. Physical evidence of degradation can be observed in FIG. 10A, particularly at the edge of the inoculated sample on the left.
Figure 10B:
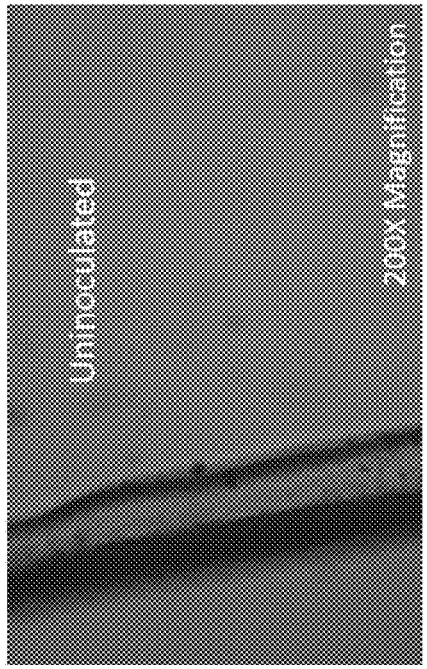
Figure 10A:
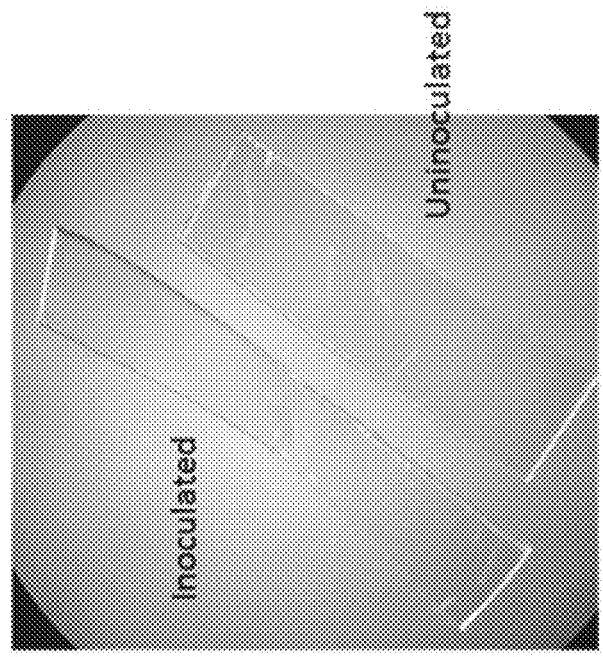

Example 15—Comparison of Consortia Bacteria and Individual Isolate Degradation of PET Further experiments were conducted to determine whether consortia bacteria were better able to degrade plastic compared to the individual isolates. Granular PET was incubated with the bacteria in carbon free medium over a 50 day period. It was observed that the full consortium, containing of all 5 isolates (isolates 9.1, 9.2, 10, 13.1, and 13.2) reduced the 100 mg granular PET pellets by 3 mg over the incubation period, a reduction of 3%, which was greater than any of the other individual and consortium isolates (see FIGS. 9A and 9B). Physical evidence of PET degradation was observed as illustrated in FIGS. 10A and 10B.

Example 16—Comparison of Individual Isolate Esterase Activity

Further experiments were performed to determine which individual isolates had non-specific esterase activity. Isolates 9.1 (*Bacillus thuringiensis* str. C15), 9.2 (*Pseudomonas* sp. B1), 10 (*Pseudomonas* sp. SWI36), 13.1 (*Bacillus albus* str. PFYN01) and 13.2 (*Pseudomonas* sp. SWI36) were grown on $CaCl_2$-Tween 20 agar to screen for esterase activity. Isolates were incubated at 26° C. for 96 hrs. Isolates 9.1, 9.2, and 13.1 all exhibited secreted esterase activity. Precipitant appears when esterases are secreted beyond the colony growth for all isolates except 10 and 13.2. The white arrow points to precipitant observed for isolate 9.2 (see FIG. 11).

It will be apparent to those having skill in the art that many changes may be made to the details of the above-described embodiments without departing from the underlying principles of the invention. The scope of the present invention should, therefore, be determined only by the following claims.

The invention claimed is:

1. A method of degrading a polymer, the method comprising incubating the polymer with a bacterial consortium comprising:
   one or more *Pseudomonads* species;
   one or more *Bacillus thuringiensis*; and
   one or more *Bacillus albus*.

2. The method of claim 1, wherein the one or more *Pseudomonads* species are *Pseudomonas* sp. SWI36 or *Pseudomonas* sp. B10.

3. The method of claim 1, wherein the one or more *Pseudomonads* species are selected from at least one of isolate 9.2 deposited as NRRL No. B-67633, isolate 10 deposited as NRRL No. B-67630, or isolate 13.2 deposited as NRRL No. B-67634.

4. The method of claim 1, wherein at least one of the one or more *Bacillus thuringiensis* is *Bacillus thuringiensis* str. C15 or wherein at least one of the one or more *Bacillus albus* is *Bacillus albus* str. PFYN01.

5. The method of claim 1, wherein at least one of the one or more *Bacillus thuringiensis* is selected from isolate 9.1 deposited as NRRL No. B-67632 or at least one of the one or more *Bacillus albus* is selected from isolate 13.1 deposited as NRRL No. B-67631.

6. The method of claim 1, wherein the polymer is selected from at least one of polyethylene terephthalate (PET), high-density polyethylene (HDPE), low-density polyethylene (LDPE), or polypropylene (PP).

7. The method of claim 1, wherein the polymer is polyethylene terephthalate (PET).

8. The method of claim 1, wherein the polymer and the bacterial consortium is incubated in a liquid carbon-free basal medium (LCFBM).

9. The method of claim 1, further comprising exposing the polymer to ultraviolet (UV) radiation.

10. The method of claim 9, wherein the polymer is exposed to the UV radiation prior to incubating the polymer with the bacterial consortium.

11. The method of claim 1, further comprising incubating the polymer and the bacterial consortium with a biosurfactant and/or a biocatalyst.

12. A method for degrading a polymer-containing substrate, the method comprising:
    obtaining a polymer-containing substrate;
    mechanically disintegrating at least a portion of the polymer-containing substrate;
    subjecting the polymer-containing substrate to ultraviolet (UV) radiation; and
    incubating the polymer-containing substrate with one or more *Pseudomonads* or *Bacillus* species, wherein the one or more *Pseudomonads* or *Bacillus* species is selected from the group of *Pseudomonas* sp. SWI36, *Pseudomonas* sp. B10, *Bacillus thuringiensis* str. C15, and *Bacillus albus* str. PFYN01.

13. The method of claim 12, further comprising incubating the polymer and the one or more *Pseudomonas* or *Bacillus* species with a biosurfactant and/or a biocatalyst.

14. The method of claim 12, wherein incubating the polymer-containing substrate with one or more *Pseudomonads* or *Bacillus* species is incubating the polymer-containing substrate with a bacterial consortium comprising *Bacillus thuringiensis* str. C15 and *Pseudomonas* sp. B10.

15. The method of claim 14, wherein the bacterial consortium further comprises *Pseudomonas* sp. SWI36, *Bacillus albus* str. PFYN01, or both.

16. A method for degrading a polymer-containing substrate, the method comprising:
    incubating the polymer-containing substrate with a bacterial consortium comprising:
    isolate 9.1 deposited as NRRL No. B-67632; and
    isolate 9.2 deposited as NRRL No. B-67633.

17. The method of claim 16, wherein the bacterial consortium further comprises isolate 10 deposited as NRRL No. B-67630, isolate 13.1 deposited as NRRL No. B-67631, isolate 13.2 deposited as NRRL No. B-67634, or combinations thereof.

18. The method of claim 16, wherein before incubating the polymer-containing substrate, the method further comprising:
    mechanically disintegrating at least a portion of the polymer-containing substrate; and
    subjecting the polymer-containing substrate to ultraviolet (UV) radiation.

* * * * *